United States Patent [19]
Kopf

[11] Patent Number: 6,127,141
[45] Date of Patent: Oct. 3, 2000

[54] CULTURE DEVICE AND METHOD

[76] Inventor: Henry B. Kopf, 108 Coatbridge Cir., Cary, N.C. 27511

[21] Appl. No.: 09/307,932

[22] Filed: May 10, 1999

Related U.S. Application Data

[63] Continuation of application No. 07/207,655, Jun. 21, 1988, which is a continuation-in-part of application No. 06/936,486, Nov. 26, 1986, Pat. No. 4,885,087.

[51] Int. Cl.[7] ........................................ C12P 1/00
[52] U.S. Cl. .................... 435/41; 435/286.5; 435/297.2; 435/297.4
[58] Field of Search ............................. 435/286.1, 286.5, 435/289.1, 293.1, 297.1, 297.4

[56] References Cited

U.S. PATENT DOCUMENTS

| | | | |
|---|---|---|---|
| 3,259,546 | 7/1966 | Polley | 167/78 |
| 3,259,547 | 7/1966 | Cole | 167/78 |
| 3,821,087 | 6/1974 | Knazek et al. | 195/127 |
| 3,919,044 | 11/1975 | Melnick et al. | 195/1.5 |
| 4,203,801 | 5/1980 | Telling et al. | 435/284 |
| 4,209,402 | 6/1980 | Gentles | 210/137 |
| 4,220,725 | 9/1980 | Knazek | 435/285 |
| 4,225,671 | 9/1980 | Puchinger et al. | 435/71 |
| 4,416,986 | 11/1983 | Markus et al. | 435/68 |
| 4,661,458 | 4/1987 | Berry et al. | 435/284 |
| 4,664,912 | 5/1987 | Wiktor et al. | 424/89 |
| 4,687,664 | 8/1987 | Philapitsch et al. | 424/85 |
| 4,804,628 | 2/1989 | Cracauer et al. | 435/240.242 |
| 4,867,876 | 9/1989 | Kopf | 210/228 |
| 4,885,087 | 12/1989 | Kopf | 210/321.72 |
| 4,886,779 | 12/1989 | Hilfenhaus | 514/2 |
| 4,889,812 | 12/1989 | Guinn | 435/289 |
| 5,868,930 | 2/1999 | Kopf | 200/321.75 |

FOREIGN PATENT DOCUMENTS

| | | |
|---|---|---|
| 0155237 | 3/1985 | European Pat. Off. . |
| 6-188872 | 7/1994 | Japan . |

OTHER PUBLICATIONS

Cheryan et al. in Mebrane Separations in Biotechnology, McGregor (ed), Marcel Dekker Inc., pp. 258–261 (1986).

New Brunswick Scientific Product Bulletin, Celltronics, HF-100. The Bench–Top Hollow Fiber Bioreactor System.

Chemical Engineer's Handbook, Fifth Edition, McGraw Hill Book Company, Liquid–Solid Systems, 1973.

*Primary Examiner*—David A. Redding
*Attorney, Agent, or Firm*—Steven J. Hultguist; William A. Barrett

[57] ABSTRACT

A culturing system and method particularly useful for producing cellular products such as viral pathogens of cells. It includes a mass transfer culture segment, stacked filter plates to adjust the medium composition, and a product removal and concentration segment. The mass transfer culture segment utilizes changed directional flow of the medium to maximize cell growth and production of product. The stacked filter plates allow addition of sterile fresh medium and removal of growth inhibitory substances.

56 Claims, 7 Drawing Sheets

CULTURE DEVICE AND METHOD

RELATED APPLICATIONS

The present application is a continuation of U.S. patent application Ser. No. 07/207,655, filed Jun. 21, 1988, which is in turn a continuation-in-part of U.S. patent application Ser. No. 06/936,486, filed Nov. 26, 1986, issued Dec. 5, 1989 as U.S. Pat. No. 4,885,087.

BACKGROUND OF THE INVENTION

1. Field of the Invention

This invention relates to a device and method for culturing pathogenic microorganisms and viruses to conserve laboratory space and avoid contamination of the culture and release of pathogens into the environment. In particular, this device pertains to a device and method for obtaining large volumes of pathogenic viruses such as the AIDS virus in a closed culture system.

2. Description of the Related Art

Pathogenic animal viruses, such as the human immunodeficiency virus (HIV), the rabies and herpes viruses, and pathogenic bacteria such as *Neisseria meningiditis* and *Mycobacteria avium* must be studied with extreme precaution to avoid spread of the virus and contamination of workers and research areas. In the following discussion of viruses, it is understood that other pathogens may be handled in analogous fashion. The problem is that in order to study these viruses, large quantities of viruses and large volumes of virus extracts must be prepared and isolated from growth media and contaminating cells, microbes and debris. Although other pathogens, such as pathogenic bacteria or yeasts do not usually require such large volumes of cell growth as are required for viruses to obtain sufficient material for study, the cells must also be cultured in quantity and handled with great care to avoid worker exposure and accidental release of the organisms.

Microbial cellular pathogens of animals such as cellular viruses generally must be cultured in growing animal cell cultures. The standard method to culture such cells is by the use of roller bottles. Roller bottles are coated on the inside by a layer of solid or semi-solid growth substrate bathed by a nutrient medium on which the cells are grown. The cell growth in roller bottles and similar growth vessels, and thus, the viral yield, are limited by the internal surface area of the glass or plastic bottle and by the nutrients in the nutrient medium. To obtain the large scale viral yields that are necessary to study viruses, the number of roller bottles needed may often fill shelves that extend from wall to wall and floor to ceiling in several growth rooms. This requires that large areas of laboratory space be allocated for incubation facilities and often necessitates construction and/or room conversion and attendant delays for those beginning to do research in this area.

The processes of preparing the large number of roller bottles, inoculating them with infected cells, incubating them under the appropriate conditions, extracting the viruses from the individual bottles, concentrating the viral suspensions, and lysing the viruses to obtain non-pathogenic viral extracts for research also are time-consuming and expensive. The numerous complicated manual manipulations required in these procedures allow many opportunities for mistakes to occur and problems to develop. Errors by the laboratory workers may result in unwarranted experimental conclusions and/or increased expenses and delays occasioned by the repeated experiments.

The multiple experimental steps involving opening of the roller bottles and the multiple number of roller bottles required increases the likelihood that some of the human host cells will be contaminated by undesirable microorganisms or viruses that may kill the host cells. This may decrease viral production of the system being studied or complicate extraction of the desired virus components from the culture.

The large volume of viral suspensions produced in the existing culture systems necessitates a massive time-consuming effort of viral harvesting. The dilute viral suspensions that are obtained from the prior culture systems are difficult to treat effectively to lyse the viruses until the suspension has been concentrated. Thus, in a typical procedure, these large volumes of infective viruses must be placed in centrifuge tubes. The supernatant fluid must be decanted, with the possibility of resuspension of the infective particles, and the pellet must then be treated to lyse the viruses.

Thus, the numerous manual procedures that are required by the prior art increases the possibility of escape of some of the pathogenic virus particles from the culture system and their release from the laboratory into the environment. It is of the highest priority that the release of pathogenic viruses such as the AIDS virus be avoided.

Mass transfer operations are often used to attempt to solve some of the problems of growing a large number of cells that are associated with culture systems such as roller bottles. In the mass transfer chamber, a biological medium may be on one side of a mass transfer surface element and the medium to which or from which mass transfer is to be effected is disposed on the opposite side of the element. Counterflow of the two media past each other effects diffusional and/or osmotic mass transfer. Problems in the prior art, which include reduction of mass transfer after prolonged operation of a mass transfer element, longitudinal decrease of mass-transfer efficiency due to fouling of mass transfer surfaces, and presence of undesirable micro-environments and areas of preferential cell growth, are substantially avoided with the cell culturing system disclosed in my copending patent application U.S. Ser. No. 06/936,486 filed Nov. 26, 1986, the entire disclosure of which is hereby incorporated by reference. This system may be used to culture cells continuously on cellular or microbead substrates with a minimum of risk.

In the culture of host cells to produce progeny viruses, even with optimized mass cell culturing systems, there remain problems of handling the culture fluid containing the viruses that is being circulated through the system. Inhibitory substances of various sizes must be removed from the media without removing the viruses to allow cell growth to continue and viral concentration to increase. There also must be a way to add new medium in order to allow cell growth to continue without increasing the volume of the culture medium that contains the virus. These purposes may be accomplished by use of the stacked filter train disclosed in my copending patent application U.S. Ser. No. 07/104,177, filed Oct. 2, 1987, the entire disclosure of which is hereby incorporated by reference, which allows media to be added or wastes to be withdrawn from a cell culture system without contamination of the system or the operator.

Even with the prior art technology, the problems remain of finding a method of culture of the cells to maximize virus yield; an arrangement of culture vessel apparatus and stacked filter train(s) to allow optimal recovery of viruses without excessive contamination by metabolites, medium components, cell debris, or other unwanted materials; and most importantly, a means by which viruses may be concentrated and lysed without causing them to be removed from the culture system to avoid all handling of the pathogenic viruses after the initial inoculation of the system.

Accordingly, it is an object of the present invention to provide an improved method and apparatus for effecting increased cell growth and pathogen yield in which release of infective pathogens is avoided.

It is another object of the invention to provided an improved method and apparatus for effecting increased cell growth and pathogen yield in which the infective pathogens are not handled by laboratory personnel after the original inoculation with the infected cells.

It is another object of the invention to provide an improved method and apparatus for effecting increased cell growth and pathogen yield by aseptic removal of spent medium components.

It is another object of the invention to provide an improved method and apparatus for effecting increased growth and pathogen yield by aseptic addition of nutrients.

It is a further object of the invention to provide a method and apparatus for effecting increased pathogen yield that occupies a minimum of laboratory space and does not require construction of special rooms or buildings.

It is another object of the invention to provide a method and apparatus for concentrating pathogen suspensions such as viral suspensions for subsequent lysis without requiring handling large volumes of infective pathogens.

It is another object of the invention to provide a cost-reducing method and apparatus for effecting increased cell growth and pathogen yield.

It is a further object of the invention to provide a sealed virus-tight, unified, preassembled apparatus for aseptically growing pathogens, monitoring and adjusting medium components, harvesting the pathogens from the medium, rendering the pathogens harmless and obtaining unhazardous pathogens or pathogen components.

Other objects and advantages of the invention will be more fully apparent from the following disclosure and appended claims.

SUMMARY OF THE INVENTION

In a broad aspect, the invention relates to a microbial culturing system closed by sterile barriers, comprising:
(a) a medium reservoir containing a medium for growing cells;
(b) a tangential flow growth device connected to the medium reservoir, said tangential flow growth device having a medium flow control means;
(c) a pump system having discharge and inlet ports for pumping the medium from the medium reservoir to the tangential flow growth device;
(d) a sterile barrier tangential flow membrane device connected to the tangential flow growth device;
(e) a means for monitoring medium conditions; and
(f) a means for harvesting culture product openably and closably connected to the tangential flow growth device. In this aspect of the invention as well as the others discussed herein, the term "microbial" comprises viruses as well as bacteria and other microbes. Similarly, because the system may be used to culture non-pathogens as well as pathogens, the term "pathogens" refers to the microbial product whether pathogen or non-pathogen unless the context indicates otherwise.

In particular, the invention relates to a closed microbial pathogen culturing system, comprising:
(a) a medium reservoir containing a growth medium,
(b) a mass transfer culture system connected to the medium reservoir, said mass transfer culture system having switchable flow control means for controlling the direction of flow of medium through the mass transfer culture system;
(c) a pump system having discharge and inlet ports for pumping the medium from the medium reservoir to the mass transfer culture system;
(d) a stacked plate filter system capable of solids filtration and connected to the mass transfer culture system;
(e) a means for nutrient exchange into and out of the medium;
(f) a means for sampling and monitoring components of the medium;
(g) a means for harvesting culture product openably and closably connected to the mass transfer culture system; and
(h) a culturing system control means for automatically controlling medium flow.

The preferred method of the invention for growing cell cultures using a closed microbial culturing system comprises the steps of:
(a) inoculating a mass transfer culture system having a switchable flow control means with cells capable of producing a desired cell product;
(b) exposing the cells to a flowing cell growth medium;
(c) periodically changing direction of flow of the cell growth medium with the switchable flow control means;
(d) adjusting medium components to optimize cell product production by means of a sterile barrier tangential flow membrane device; and
(e) filtratingly concentrating the cell product by removal of liquid from the medium without removing cell product from the microbial culturing system.

In the mass transfer culture system of the preferred embodiment of the invention, a four-way valve is used to control the direction of flow of the medium. Thus the circulating medium may be reversed in direction of flow without the need for changes in the inlet and outlet ports. The change in the direction of flow causes a better mixing of the extracapillary volume, which aids in the diffusion of the nutrients required for growth, to the cells, and in the diffusion of growth inhibitory substances away from the cells. The four-way valve may be a manually operated device switched periodically, or more appropriately, an automated device switchable by a timed signal from a remote controller. Four-way valves suitable for use in the invention are currently available from Quality Controls (Tilton, N.H.) and Alpha Larval (Kenosha, Wis.).

Tangential flow devices used in the invention for growing cells and for adjustment of medium component concentrations comprise nonrestrictive sterile barriers for the metabolites of cell growth. In addition, they have a low coefficient for absorption and adsorption of the cellular metabolites.

In addition to the particular preferred embodiments of the mass transfer culture system and the stacked plate filter system discussed below, the tangential flow devices may comprise a mass transfer culture system utilizing a hollow fiber device as marketed by Amicon Corporation (Danvers, Mass.) or Microgon Corp. (Laguna Hills, Calif.) or plate and frame devices such as Minitan® or Pellicon Cassette ®

(Millipore Corp., Bedford, Mass.). Thus, a hollow fiber device such as the stainless steel Microgon® equipped with a 0.2 micron hydrophilic membrane may be used for small to medium volume (1000 ml) applications. A typical tangential flow device for cell culture will include a filter having 0.2 micron diameter or smaller pores, configured to assure continued operation over the lifetime of the culture for the purposes of sampling, for example, for glucose and lactic acid or collection of expressed proteins, IgG or growth hormones, and replenishment of the growth medium without loss of sterility in the recirculating loop.

A preferred filter system component that may be used in this invention is disclosed in U.S. patent application Ser. No. 07/104,177, referred to above, and comprises stacked filter plates forming a cross-flow filter and is capable of substantially uniform transverse distribution of inflowing liquid from a feed port and highly uniform liquid cross-flow across the full transverse extent of the flow channel. Each filter plate has on the inlet side, a transverse liquid feed trough and on the outlet side, a liquid collection trough. Between the liquid feed trough and the liquid collection trough is a plurality of parallel partitions that define subchannels and are of a lesser height than a wall that circumscribes the flow channel that is between the two troughs.

Filter plates as disclosed above may be utilized in stacked pairs to form enclosed flow channels within which efficient filtration may occur. A first plate of the stacked pair is paired with a second plate that is a mirror image of the first plate positioned in an inverted relationship to the first plate such that the respective circumscribingly bounding walls of the first and second plates are in abuttingly sealing contact with one another. Between the adjacent stacked plates is placed a foraminous support of the general rectangular dimensions of the flow channel, with filter sheet elements between the foraminous support and each of the paired plates. The foraminous support functions to positionally retain the filter on either side thereof and to accommodate the interior flow of solids-depleted liquid toward the filtrate collection means associated with the filter plate.

In operation of the stacked filter plate assembly, liquid is introduced via the liquid inlet port. The liquid enters the liquid feed trough and is laterally distributed from the medial portion of the feed trough into the subchannels and toward its outer extremities in a highly uniform flow over the full areal extent of the sheet filter elements. This structure results in an increased solids filtration capacity and extended operation time and thus a higher microbial or virus yield may be obtained before the filter must be regenerated or changed.

In lieu of the foraminous support, a filter element comprising a support may be employed that includes a circumscribing frame with an array of spaced-apart and substantially parallelly aligned ribs extending and joined at their opposite ends to the frame so that the ribs form a series of correspondingly substantially parallel filter plate flow channels. Openings in the frame allow liquid flow communication with the filtrate flow channels for egress of filtrate from the filtrate flow channels. A first filter sheet is secured to one face of the frame and a second filter sheet is secured to the second face of the frame. Together the filter sheets and the frame define an enclosed interior volume comprising the filtrate flow channels separated by the ribs. Filtrate enters the enclosed liquid volume of the filter through the first and second filter sheets and is able to flow in the filtrate flow channels and be discharged from the filter element through the frame openings. Employment of a series of filter trains allows washing of the cells, desalting of the medium, and finally, concentration of the viruses (dewatering).

The filter element may be formed as a conventional wire screen, a sintered metal plate or any other construction providing the requisite supportive function for the filter sheets and accommodating flow between the filter sheets toward the liquid filtrate collection and discharge means.

The preferred mass transfer culture system to be used in this invention has a switchable flow control means comprising a four-way valve enabling the direction of fluid flow to be reversed by activation of the valve. Such a mass transfer culture system is disclosed in my pending patent application (Ser. No. 06/936,486) and is discussed below as used in the pathogen culturing system of the invention disclosed herein. Growth of host cells occurs in one mass transfer medium in the hollow fiber membrane while fresh culture medium comprises a second mass transfer medium.

In use with the invention, one or more mass transfer chambers connected to a pump are linearly connected by means of tubing to one or more stacked plate filters and to a viral harvest means. The mass transfer chambers are inoculated with a cell culture. The cells are either previously infected with a pathogen or are inoculated after placement in the chambers. The cells are bathed with fresh medium from the medium reservoir. As metabolic waste products are accumulated in the spent medium, they are removed by a stacked plate filter.

When the pathogen concentration has reached the desired level, and the viral suspension has been concentrated such as through use of a stacked filter plate, the concentrated suspension is allowed to enter the viral lysis chamber by means of a valve. Appropriate lysing agent is aseptically added to the viral suspension and after incubation to ensure complete lysis, the inactivated pathogen components may be removed from the system. It may not be necessary to use this lysis step when non-pathogens are grown in this culturing system.

The entire culturing system may be constructed to occupy a space of 4×4×6 feet to allow harvest of about $10^8$ to $10^{10}$ cells per ml. Due to the compact and efficient nature of the invention, the following yield is obtained with the invention. An appropriate volume starting is approximately 100 liters of medium, depending on the type of cells to be grown and the efficiency of medium utilization of cells. This volume has the same pathogen production capability as about 1000 roller bottles having one liter of medium each. Such roller bottles may, for example, produce $10^6$ cells per ml or $10^9$ cells per bottle. In the culture system of the invention, 100 liters of medium are added to the system and about 99 liters of fluid are removed prior to addition of the concentrated pathogen suspension to the harvest vessel. The final pathogen producing cell density may be about $10^{10}$–$10^{12}$ pathogens per ml in the final 1-liter harvest vessel. The host cells are thus somewhat more productive per volume of medium used in the culture system of the invention than in the prior culture systems. More significantly, a substantially higher pathogen concentration may be obtained using the invention without the costly, hazardous, time-consuming and space-consuming roller bottle system. The result with the invention is increased personnel efficiency and safety at decreased cost in about one one-thousandth of the laboratory space.

Other aspects and features of the invention will be more fully apparent from the description set forth hereinafter.

DETAILED DESCRIPTION OF THE INVENTION AND PREFERRED EMBODIMENTS THEREOF

The present invention comprises a pathogen culturing system in which a pathogen such as a cellular virus may be grown to high concentrations in a closed system using a mass transfer culture system and a series of stacked filter plates. After the appropriate number of pathogens has been produced, the pathogen may be separated from the host cells, growth medium constituents and unwanted growth products, and then be concentrated and treated to lyse the pathogen without opening the system or risking release of the pathogen.

FIGS. 1–4 depict more detailed features of the mass transfer culture system. FIGS. 5–14 show details of the stacked plate filter system. The whole pathogen culturing system of the invention is shown schematically in FIG. 15.

Medium Reservoir and Pump

Figure 1:
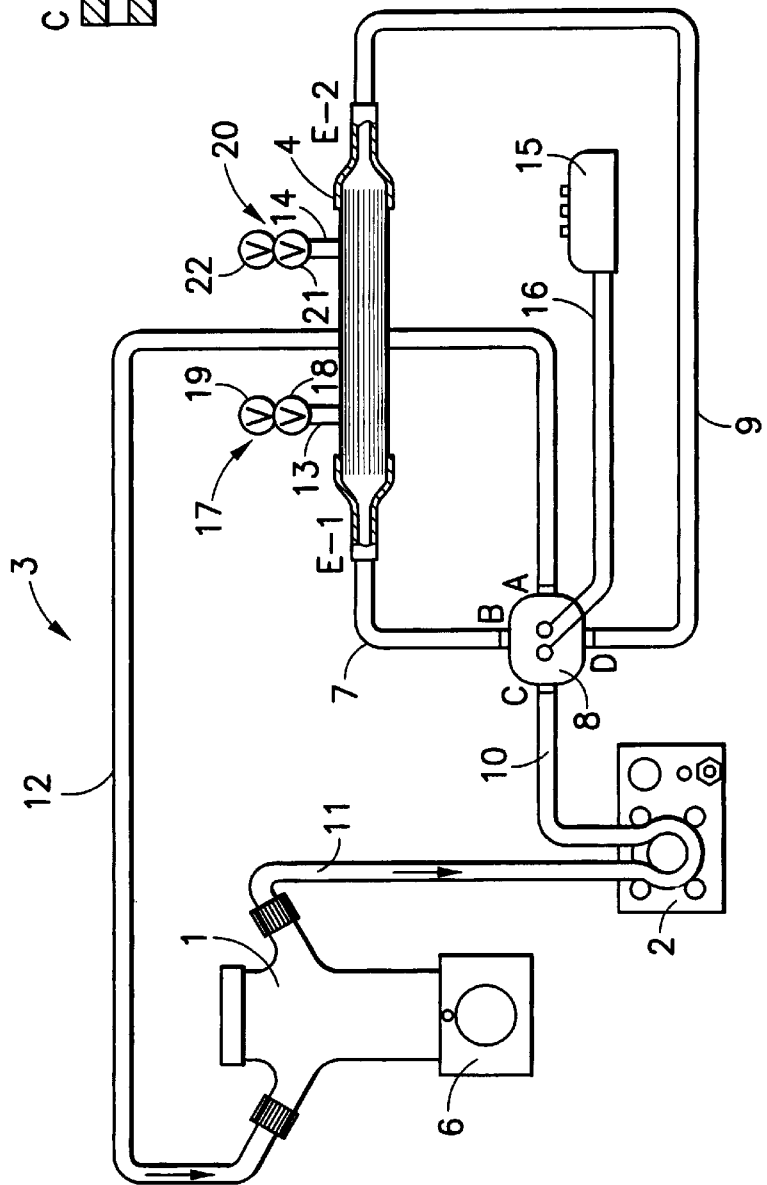
FIG. 1 is a schematic diagram of a mass transfer system component that may be used in the invention.

The medium reservoir 1 is preferably a vessel of stainless steel or other durable easily sterilizable material capable of holding 100 to 1000 liters of medium. Such reservoir may be of a type commercially available from the Walker Stainless Equipment, New Lisbon, Wis. As shown in FIG. 1, a variable speed pump 2 is connected to the medium reservoir 1 and mass transfer culture system 3. The pump 2 may comprise a peristaltic pump as shown in FIG. 1, such as is commercially available from Cole-Palmer Company, Chicago, Ill., or a variable speed gear pump, such as the MICROPUMP® gear pump, commercially available from the Micropump Corporation, Concord, Calif. A positive displacement lobe pump may also be used (Waukesha Pump Co., Waukesha, Wis.).

The medium reservoir 1 may be equipped with stirring or agitation means to promote uniform distribution of medium components, such as a magnetic stirrer, an internal agitator, or a bottom mounted, magnetically coupled agitator as is made by APCO Technologies (Vancouver, Wash.). As shown in FIG. 1, the medium reservoir 1 is disposed on a magnetic stirrer device 6 which provides agitation of the contents of the reservoir 1. The magnetic stirrer 6 may suitably be of a type having a variable speed, to provide a varying level of agitation in the reservoir 1 depending on the density and suspension characteristics of the nutrient medium contained therein. The medium reservoir may also be provided with a medium pH monitoring and adjustment means or other means for adjustment of medium components or conditions of incubation according to means and devices known in the art. The temperature of the medium reservoir 1 may be varied depending on the desired cell growth conditions. Medium reservoir(s) may be associated with a temperature control unit, may be placed in a controlled temperature environment or may be left at ambient temperature.

Mass Transfer Culture System

A mass transfer culture system 3 is shown in FIG. 1 that may be employed for cell growth processes and for desalting and harvesting of cellular products including viruses and utilizing a hollow fiber membrane 4 of conventional type. The hollow fiber membrane 4 provides a first set of interior passages in constituent hollow fibers 5 through which a first medium, supplied from medium reservoir 1, is flowed. The internal diameter of individual fibers in the bundle may for example be from about 0.25 to about 1 mm, with pores for diffusional and/or osmolytic transfer of nutrient species, in the wall of the tubular fibers, of about 0.2 micron diameter. Such bundles are typically potted at their ends in urethane or epoxy resins, so that they may be suitably headered to accommodate flow through the interior passages of the hollow fibers, without leakage into the interstitial passages. The nutrient thus is flowed longitudinally through the interior passages of the hollow fibers, and nutrient species transfuse through the fiber walls to the cellular culture contained in the interstitial passages of the bundle. Illustrative hollow fiber membrane mass transfer elements suited to the practice of the invention are made by A/G Technologies, Needam, Mass., and CD Medical Corporation, Miami, Fla.

The hollow fiber membrane 4 is connected at one end, designated E-1, by conduit 7 to a port designated B, which is one of four such ports, the others being designated A, C, and D, of a four way valve 8. The conduit 7 may be flexible, elastic silicone tubing, or may be formed of a more rigid material such as 316 stainless steel tubing. The opposite end of the hollow fiber membrane 4, designated E-2, is connected by conduit 9 to port D of the 4-way valve 8. A 4-way LL valve 8 generally useful in the broad practice of the invention is manufactured by Quality Controls Company, Tilton, N.H.

Pump 2 is connected on its discharge side by conduit 10 to port C of the 4-way valve 8. The inlet side of pump 2 is connected by conduit 11 to the outlet port of a reservoir 1 containing the nutrient medium for the culture system. The inlet end of the reservoir 1 is connected through another conduit 12 to port A of the 4-way valve 8.

The mass transfer chamber 3 comprising the hollow fiber membrane 4 also features a first port 3 in proximity to inlet E-1, and a second port 14 proximate to inlet E-2. These ports may be provided with suitable closure means, or may be joined with suitable flow circuitry, as hereinafter described in greater detail, for circulation of the cellular medium contained in the hollow fiber membrane 4.

4-way valve 8 has two positions. In a first position, shown schematically in FIG. 2, port C is connected to port D and port B is connected to port A. In this mode, the nutrient broth in conduit 11 from reservoir 1 is flowed by pump 2 into conduit 10, from which it enters port C, discharges through port D into conduit 9 and enters the hollow fiber membrane 4 at its inlet designated E-2. At the same time the contacted nutrient broth exits through the opposite end, designated as inlet E-2, of the mass transfer chamber 3 and passes through ports B and A of 4-way valve 8 to be returned through conduit 12 to the inlet of reservoir 1, from which the nutrient medium is circulated in the previously described manner.

When the 4-way valve 8 is in a second position (FIG. 3), port C is connected to port B and thus the valve discharges the nutrient broth into conduit 7 from which it enters the mass transfer chamber 3 containing the hollow fiber membrane 4, at the inlet designated E-1, passes through the interior passages of the hollow fibers and exits at the opposite end of the mass transfer chamber 3, designated E-2, for return in conduit 9 through ports D and A of 4-way valve 8 and conduit 12 to the reservoir 1.

Figure 2:
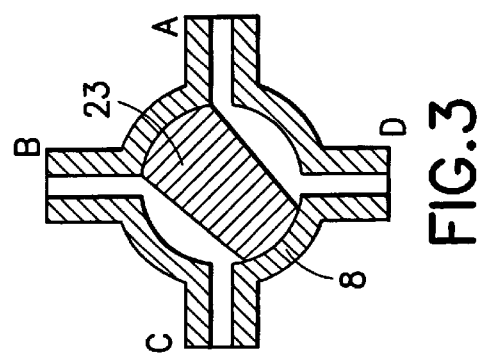
FIG. 2 is a schematic diagram of the four-way valve in a first position.
Figure 3:
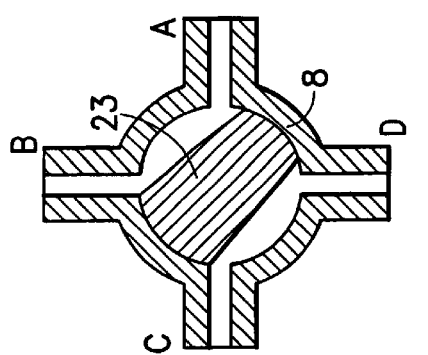
FIG. 3 is a schematic diagram of the four-way valve in a second position.

FIG. 3 further shows the 4-way valve 8 in a first position, in which the interior element 23 of the valve 8 is oriented so that valve ports B and A are in flow communication with one another, and ports C and D are in flow communication with each other. By a 90° rotation of the valve element 23, the configuration shown in FIG. 4, designated as the second position, is achieved. In this position, valve ports B and C are in fluid communication with one another, while flow communication is likewise established between ports A and D. Alternation of the valve position between the respective configurations shown in FIGS. 3 and 4 effects a cyclic alternating switching of the nutrient medium flow to the respective ends of the mass transfer chamber 3 containing hollow fiber membrane 4.

Switching of the 4-way valve 8 may be accomplished either manually or through an automatic actuator such as is schematically illustrated in FIG. 1, in which the valve 8 is controlled by a suitable automatic controller 15, operatively connected to the valve assembly by control signal wires 16. The continued operation of the system with either manual or automatic repositioning of the valve 8 results in a balanced delivery of nutrients to the mass transfer chamber alternately from its respective ends and also enhances the transport of metabolic wastes away from the cells. Further, the increased agitation incident to the switching of nutrient flows results in a more homogeneous environment with respect to other metabolic parameters.

The mass transfer culture system may also be provided at each of the ports 13 and 14, with two valves in series. At the first port 13, the valve assembly 17 comprises a first valve 18 contiguous to the port, and a second valve 19 connected in series with the first valve 18, as shown. A similar construction is employed at second port 14, where the double valve assembly 20 comprises a first valve 21 and a second outer valve 22.

The double valve arrangement described in the preceding paragraph is highly preferred in practice, since it permits cellular inoculation of the interstitial passages in the hollow fiber bundle, as well as withdrawal of the product cell culture from the interstitial passages, in a manner enabling complete sterility of the apparatus to be maintained. In the prior practice of utilizing ported hollow fiber cell growth chambers, where only one valve has been employed on each port, the introduction to or withdrawal from the mass transfer chamber of the cellular medium results in loss of sterility of the valve's interior surfaces, raising the potential for contamination of the mass transfer chamber, unless the apparatus is thereupon fully shut down, and the valves removed and autoclaved. Although some attempts have been made in the past to sterilize single-valved ports by directing super-heated steam against the valve body structure, such mode of sterilization does not reach the interior surfaces of the valve, which must be closed to retain the contents in the mass transfer chamber.

By contrast, the double valve arrangement shown permits ready sterilization of the valve assembly in a manner which preserves the sterility of the associated apparatus, by the simple expedient of opening the outermost valve (19, or 22) while the corresponding inner valve (18, or 21) is kept closed, and superheated steam, or other sterilant, is directed into the opened outer valve, to effect complete sterilization thereof. Thus, a sterile barrier is maintained at the mass transfer chamber 3 even during continuous operation, and without the necessity of shutting down the apparatus for autoclaving of the valve elements.

Figure 4:
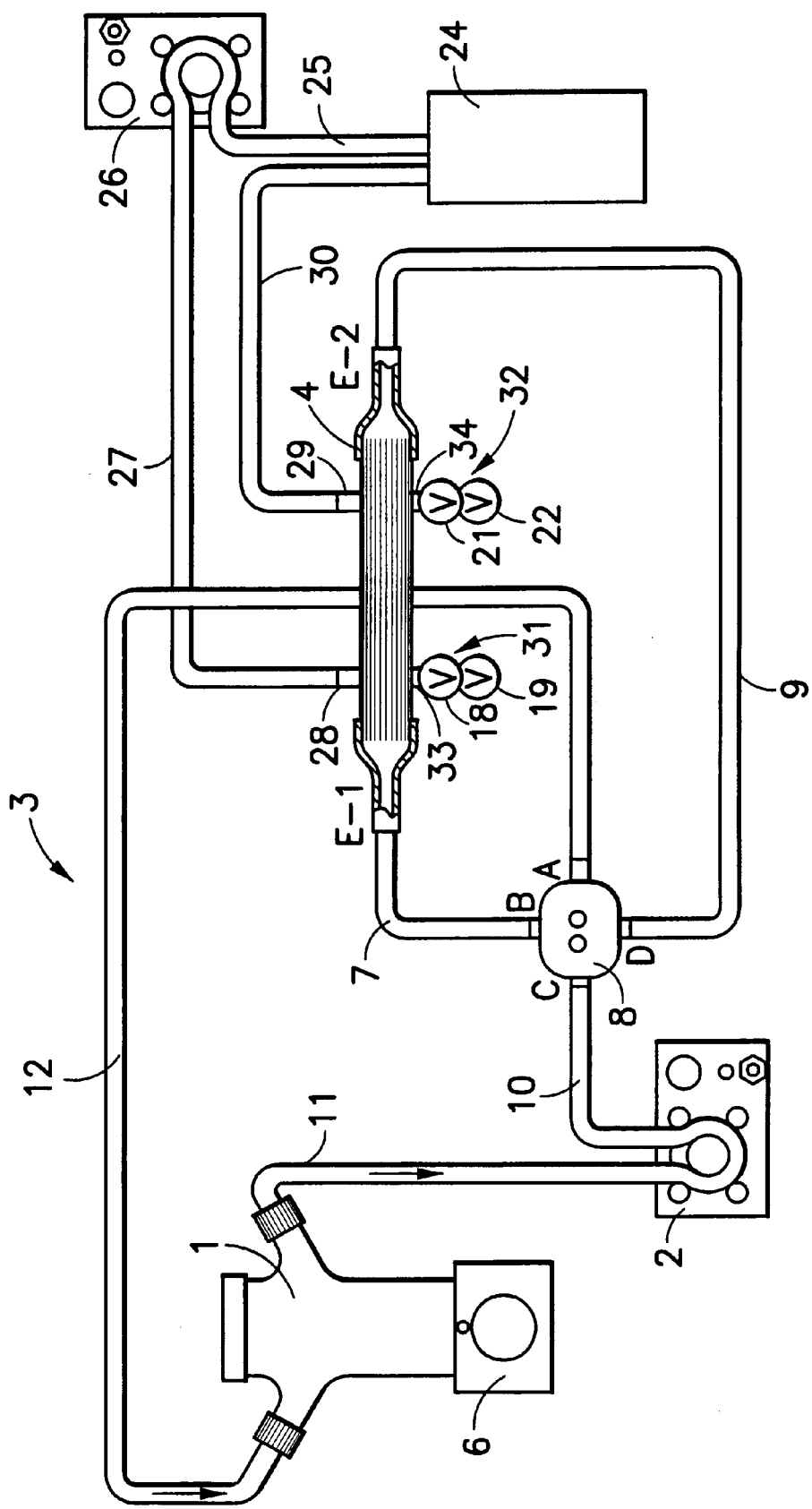
FIG. 4 is another schematic diagram of a mass transfer system component that may be used in the invention.

Concurrently, as shown in FIG. 4, with flow of the first mass transfer medium, a second mass transfer medium stored in second reservoir 24, may be withdrawn in conduit 25, passed to peristaltic pump 26, and discharged into conduit 27 from which it enters the mass transfer chamber 3 at port 28 and longitudinally flows through the interstitial passages in the hollow fiber bundle. After such longitudinal flow, in which the second medium is contacted with the first mass transfer medium concurrently flowed through the interior passages of the hollow fiber bundle, the contacted second medium is discharged from the mass transfer chamber in port 29 and flowed in conduit 30 back to second reservoir 24. A sterile barrier at the mass transfer chamber may be provided by double valve assemblies 31 and 32, as shown on the third and fourth ports, 33 and 34, respectively, of the mass transfer chamber 3 as discussed in detail above with respect to the first reservoir 1. (The analogous valves in these valve assemblies are designated by the same numbers in FIG. 4.)

Although the mass transfer chamber 3 has been described with specific reference to a hollow fiber bundle as the mass transfer surface element, it is within the purview of the invention to utilize other mass transfer elements, such as planar membranes, through which mass transfer may be effected, it being further understood that the number of specific passages within the mass transfer chamber and the number of mass transfer chambers employed may be varied widely depending on the specific mass transfer media and application employed. Use of multiple mass transfer chambers is described in pending application Ser. No. 06/936,486, referred to above.

Stacked Plate Filter System

Figure 5:
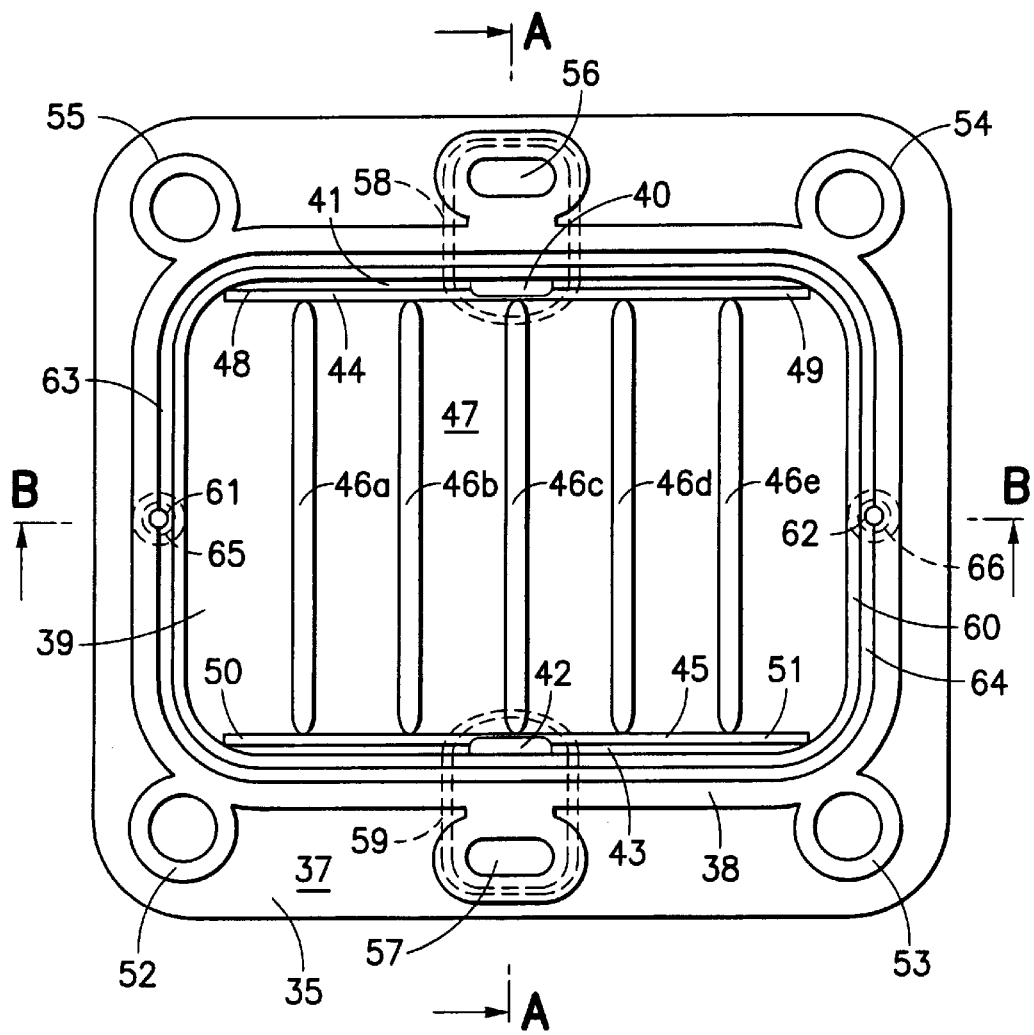
FIG. 5 is a top plan view of a filter plate component of the invention.
Figure 6:
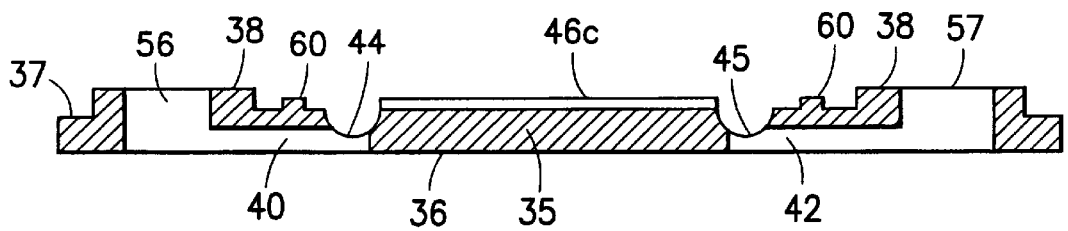
FIG. 6 is a sectional elevation view of the filter plate of FIG. 5, taken along line A—A thereof.

The stacked filter plate system component of the invention comprises one or more filters similar to those disclosed in my earlier patent application. FIG. 5 shows an illustrative filter plate in plan view. FIG. 6 shows a sectional elevation view of the FIG. 1 plate, taken along line A—A thereof, and FIG. 7 is a sectional elevation view of the FIG. 5 plate, taken along B—B thereof.

Figure 7:
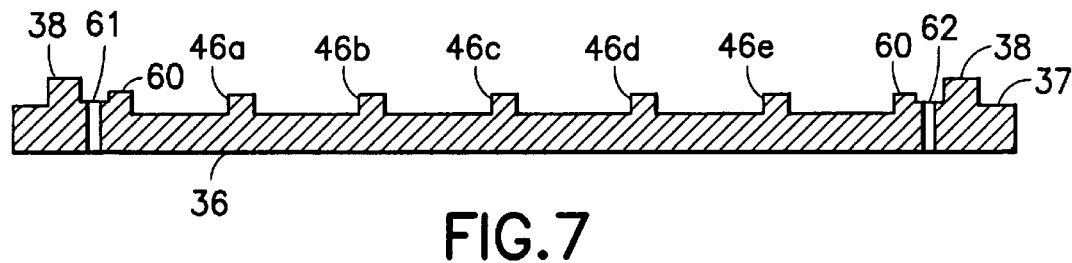
FIG. 7 is a sectional elevational view of the filter plate of FIG. 5, taken along line B—B thereof.

Each filter comprises pairs of filter plates, each plate member 35 having a generally planar and rectangular shape with a substantially flat bottom surface 36 as shown in FIGS. 5–7. The top surface 37 of the plate has an upwardly extending wall 38 circumscribingly bounding a generally rectangular flow channel 39.

The flow channel 39 of each filter plate has a liquid inlet port 40 at a medial part on a first side 41 of the flow channel 39 and a liquid outlet port 42 at a medial part on a second side 43 of the flow channel 39 opposite the first side 41. The liquid inlet port 40 is joined in liquid flow communication with a liquid feed trough 44 extending transversely across the first side 41 of the flow channel 39, and the liquid outlet port 42 is joined in liquid flow communication with a liquid collection trough 45 extending transversely across the second side 43 of the flow channel 39.

There are a plurality of spaced-apart partitions 46a, 46b, 46c, 46d and 46e, extending upwardly from the floor 47 of the flow channel 39 between the liquid feed trough 44 and the liquid collection trough 45. The partitions 46a–46e are of a lesser height than the wall 38 circumscribing the flow channel 39 and are substantially parallel to one another to define a series of sub-channels extending longitudinally between the liquid feed trough 44 and the liquid collection trough 45.

The liquid feed trough 44 and the liquid collection trough 45 each decrease in depth from their respective medial portions in communication with the liquid inlet port 40 and outlet port 42, respectively, to their marginal extremities 48 and 49, and 50 and 51, respectively.

The outer circumscribing wall 38 may as shown be formed with integral cylindrical flanges 52, 53, 54, and 55, each of which circumscribes a circular opening in the periphery of the plate to accommodate the positioning of the plate on spaced-apart rods, as hereinafter shown with reference to FIG. 10 hereof.

At the medial portions of the first and second sides of the plate, there are provided respective oblong openings 56 and 57 to accommodated the liquid feed and liquid withdrawal conduits which are employed to introduce liquid to and remove liquid from the flow channels defined by adjacently paired stacked plates. Such feed and discharge liquid conduits are more fully shown and described with reference to FIG. 6 herein. The respective liquid feed and discharge conduits are suitably formed with spaced-apart perforations therein which permit egress or ingress of liquid into or out of the flow channel via the above-described respective liquid inlet and outlet ports of the plate. In order to assure positive sealing of the flow channels and adjacently positioned plates relative to the liquid feed and discharge conduits, the liquid inlet and outlet ports of the plate are suitably provided with gasket elements 58 and 59 as shown in FIG. 1, at the bottom surface 36 of the plate.

As an example of plate dimensional characteristics for an illustrative embodiment of the invention, a filter plate suitable of filtration of aqueous biomass suspensions may be generally of square shape as shown in FIG. 1 with sides on the order of about 6 inches long, and with feed and collection troughs 44 and 45 which are each 2 millimeters deep at their medial portions, continuously decreasing to a depth of 1.5 millimeters at their respective extremities (peripheral portions 48 and 49 of feed trough 44, and peripheral portions 50 and 51 of collection trough 45). The transverse dimension (width) of each of the sub-channels defined by the partition walls 46a–e is approximately 2 centimeters.

The details of the plate construction are shown in FIG. 6 with respect to the structural features of the liquid inlet port 40 and liquid outlet port 42. The filter plate may be provided with a circumscribing main wall 38 and an interior circumscribing wall 60 of lesser height than the main wall. Between these respective walls is formed a circumscribing channel (see FIGS. 2 and 3), into which suitable openings 61 and 62 may communicate as shown in FIGS. 5 and 7. These respective openings are usefully employed as filtrate (permeate) flow channels to convey or drain the solids-depleted filtered liquid or other permeate from the stacked plate assembly.

Openings 61 and 62 may also be usefully employed as gas flow openings to assist in draining the stacked plate filter upon cessation of normal operation for regeneration. Thus, when the filter is shut down, gas from a suitable supply source (not shown) may be introduced in openings 61 and/or 62 to pressurize the flow channel 39 to a sufficient extent where the same can be drained of accumulated biomass suspension upon the termination of normal liquid flows through the system. Similarly, these respective openings may be employed for introduction and egress of steam for steam sterilization of the system or for flowing a chemical sterilant through the flow channel 39 prior to initiation or re-initiation of normal filtration operation.

Figure 11:
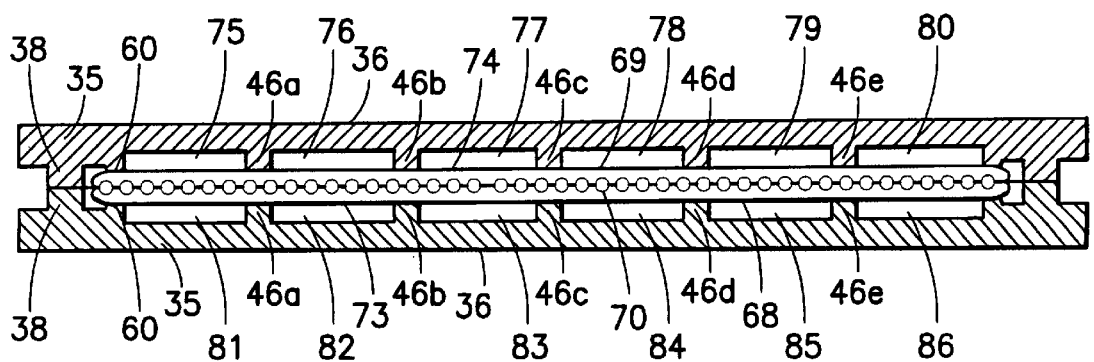
FIG. 11 is a transverse sectional elevation view of a stacked plate filter assembly component of the invention.

Further, because the edges of the foraminous support are disposed in the channel between bounding walls 60 and 38, as shown in FIG. 11, described more fully hereinafter, it is also possible to utilize openings 61 and 62 as respective secondary fluid inlet and discharge passages, for flowing a secondary fluid through the foraminous support for mass transfer contacting of the liquid introduced into the flow channel 39 from inlet port 40 and discharged from the flow channel in outlet port 42. For such purpose, it may be advantageous to "block" the channel between bounding walls 60 and 38, at symmetrically opposed regions, as shown in FIG. 5, where channel blocking segment 63 is disposed in the channel along the side thereof containing opening 61, and channel blocking segment 64 is similarly disposed in the channel proximate to opening 62. With such arrangement, fluid entering in opening 61 is diverted downwardly in the channel as shown in the drawing and across the lower portion of the channel as shown until it encounters the channel blocking element 64. Subsequently, when the fluid so introduced is issued from the edges of the foraminous support into the opposite portion of the channel as shown, it flows to outlet opening 62.

Openings 61 and 62 may be appropriately sealed between adjacent plates by provision of suitable gasket means 65 and 66, respectively, at the flat bottom surface 36 of the plate, as shown in dotted line representation in FIG. 5.

Figure 8:
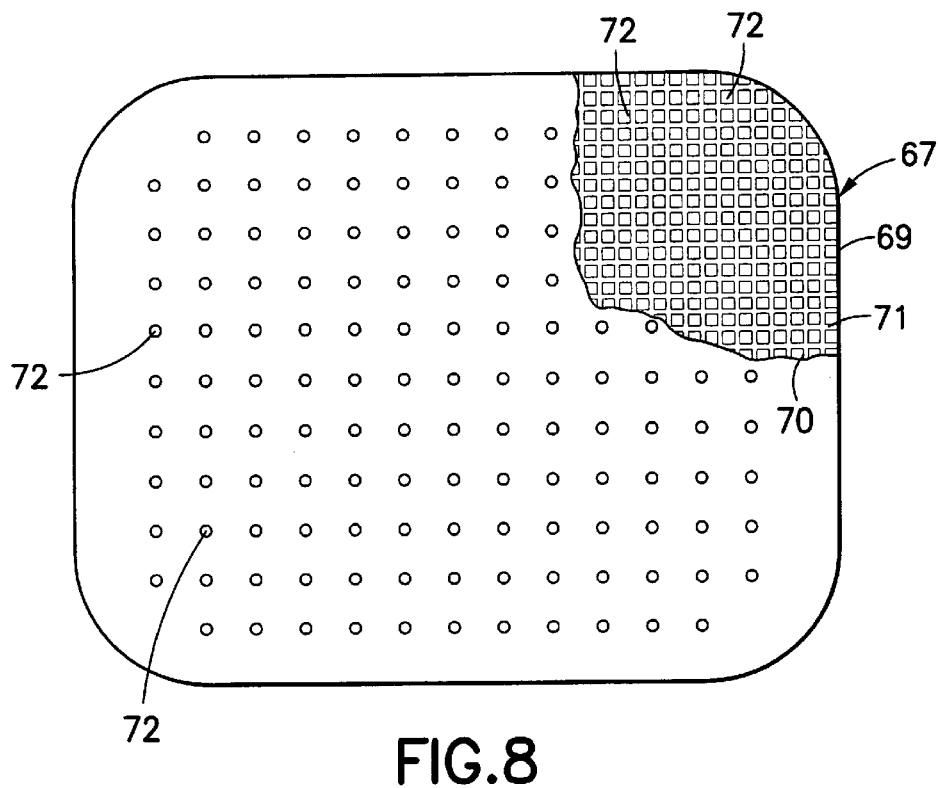
FIG. 8 is a top plan view of a foraminous support suitable for use with paired plates in the stack plate fliter assembly component of the invention.
Figure 9:
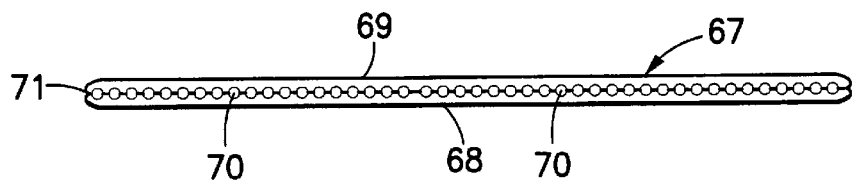
FIG. 9 is an edge elevation view of the foraminous support of FIG. 8.

FIGS. 8 and 9 show respective top plan and edge views of an illustrative foraminous support element for the stacked plate filter assembly. The foraminous support 67 is simply a support element of generally rectangular shape which is supportively reposable at a first face 68 thereof on the partitions 46a–46e and the circumscribing wall 60 of the plate element, with a first filter sheet, e.g. a filter paper sheet, therebetween.

The foraminous support 67 is likewise supportively reposable at a second face 69 thereof on the partitions and inner bounding wall of a complementary filter plate paired with the filter plate against which the first face 68 of the support is reposed. The second face 69 of the foraminous support 67 likewise has a sheet filter element between its surface and the partitions of the adjacent plate member.

The foraminous support 67 is formed with a plurality of longitudinally extending interior liquid flow channels 70 and a plurality of transversely extending interior liquid flow channels 71, wherein the longitudinal and transverse channels criss-cross one another to establish an extended interconnected network for liquid flow through the interior of the support element. Concurrently connecting the internal liquid flow network with the top and bottom foraminous support surfaces 68 and 69 on which sheets of filter paper or other filtration sheet members are mounted, is an array of surface openings 72. Thus, when a sheet of filter paper is provided for example on the top surface 69 of the foraminous support 67, the liquid (permeate) component of the solids-liquid suspension passes through the filter paper and openings 72 into the interior liquid flow network comprising channels 70 and 71, for flow through the foraminous support 67 to the edge regions thereof, where the solids-depleted liquid filtrate issues from the support into the channel between bounding walls 38 and 24 and may be removed via openings 61 and 62.

FIG. 11 is a transverse sectional elevation view of a stacked plate filter assembly component of the invention, showing the arrangement of the constituent parts thereof in which the identical complementary upper and lower plates are mated to one another. To insure positive sealing, suitable gaskets (not shown) may be interposed (e.g., in opposing grooves) between the abutting top surfaces of the respective opposed bounding walls 38. A lower filter 73 is disposed between the lower surface 68 of the foraminous support 67 and the partition bearing surface of the lower filter plate. Likewise, an upper filter sheet 74 is interposed between the top surface 69 of the foraminous support 67 and the partition bearing surfaces of the upper filter plate.

By this arrangement, there is formed a series of sub-channels 75–80 between the upper filter sheet 74 and the upper filter plate, while correspondingly a series of sub-channels 81–86 are formed between the lower filter sheet 73 and the lower filter plate, with the sub-channels being longitudinally bounded by the respective partition walls 46a–46e, as shown.

Although the foraminous support 67 has been shown as a structural element of mat-like form, the function of the support is merely to retain the filter sheet positionally on either side thereof and to accommodate the interior flow of solids-depleted liquid toward the filtrate (permeate) collection means associated with the filter plate.

The filter plates and foraminous support may be formed of any suitable materials of construction, including plastics such as polypropylene, polyethylene, polysulfone, polyimides, etc.; ceramics; metals such as stainless steels; and polymeric fluorocarbons such as polytetrafluoroethylene. Preferably the materials used are capable of withstanding sterilization for regeneration and reuse such as by high-temperatures, steam sterilization and/or chemical sanitization. Thus, the foraminous support may comprise a sintered ceramic material, e.g., of alumina, zirconia, etc., having an internal network of interconnected voids with an average void passage diameter on the order of about 1 micron. Such support may have a total void space on the order of from about 50 to about 90% by volume, e.g., about 80% voids. Further, it is to be recognized that such sintered ceramic plate may be glazed or otherwise treated on selected portions of its surface to render it liquid impermeable in such regions. Thus, the sintered ceramic plate could be selectively glazed to provide for flow through the interior thereof of a second fluid, e.g., a dialysis fluid for desalting of proteins, amino acids, and/or other biological substances being contacted with the filter sheets supported on such sintered plate.

Figure 10:
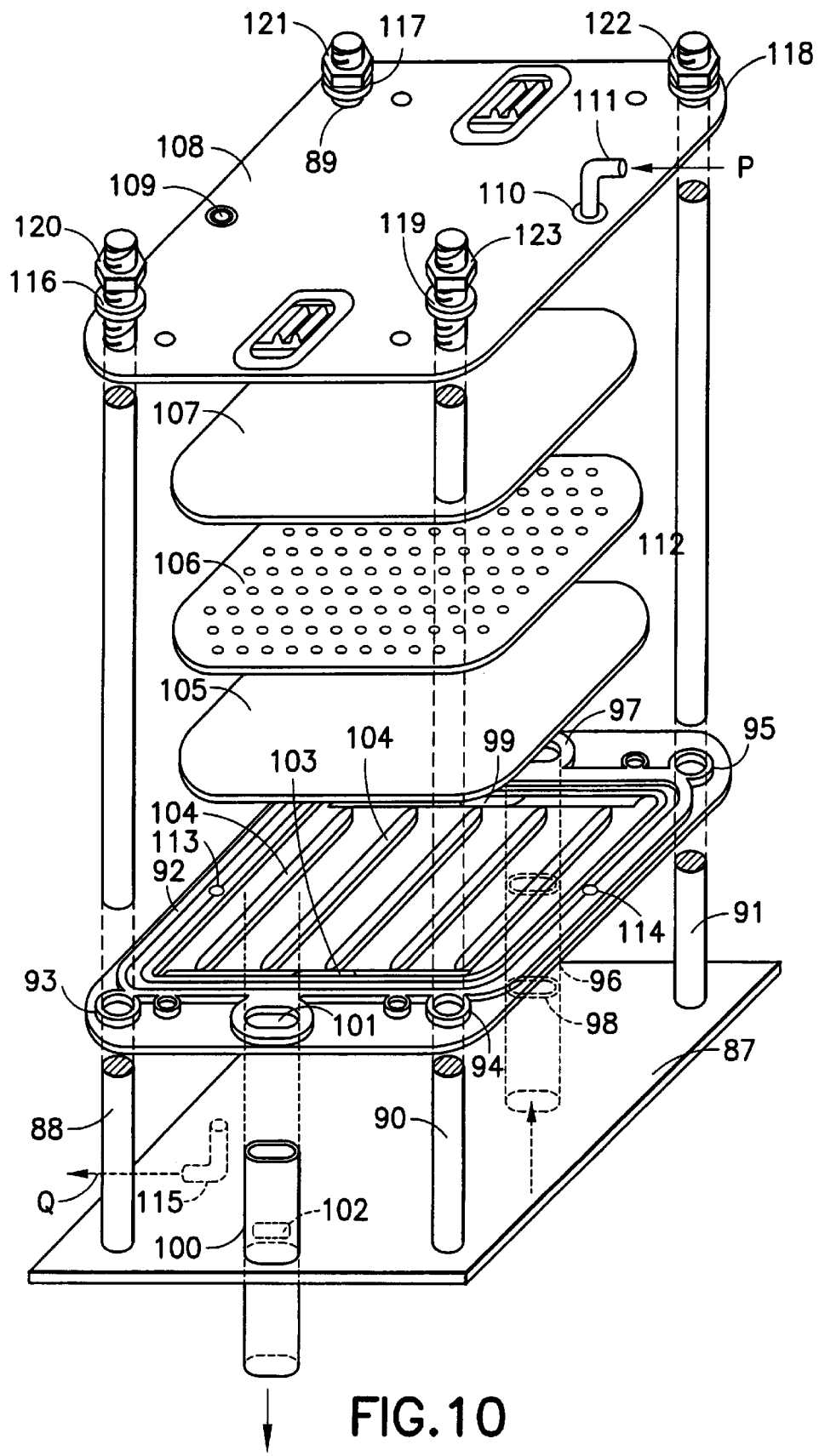
FIG. 10 is an exploded perspective view of a stacked plate filter assembly component of the invention.

FIG. 10 shows an exploded, perspective view of a stacked plate filter according to the present invention, as disposed on a base comprising a mounting plate 87 having vertically upwardly extending rods 88–91 at its respective corner portions. Mounted on the base as a lowermost element of the stack, is a filter plate 92 of the type shown in FIGS. 5–7. The respective rods 88, 90, and 91 extend through the circular openings in the plate which are surrounded by the respective cylindrical flanges 93, 94, and 95 (a similar flanged opening, not visible in this view, is provided for rod 89). The liquid feed conduit 96 for the filter extends through an opening in the base mounting plate 87 and through the liquid inlet opening 97 of the plate member, so that when filter plate 92 is in position, the liquid feed opening 98 is in register with the liquid inlet opening 97 and liquid inlet port 99 of the filter plate.

In like manner, the liquid withdrawal conduit 100 extends through a corresponding opening in the base plate 87 and liquid outlet openings 101, whereby the liquid discharge opening 102 in conduit 100 is brought into register with liquid outlet port 103 when the bottom filter plate 92 is properly positioned.

Reposed on the upper bearing surfaces of the partition walls 104 of the bottom filter plate 92 is a filter sheet 105. The filter sheet 105 may be a paper filter sheet, comprising a non-woven web of cellulosic fibers, or any other replaceable or disposable filtration medium commonly provided in sheet form and which is readily cut or otherwise shaped to the form required in the filter of the present invention. A particularly advantageous filter sheet in filter systems of the type envisioned by the present invention are polysulfone filter sheets which are readily commercially available.

Overlying the filter sheet 105 is the foraminous support 106, which is of the form illustratively shown and described with reference to FIGS. 8–9 herein. Overlying the foraminous support 106 is filter sheet 107, which may be identical in shape and construction to filter sheet 105.

Overlying the upper filter sheet 107 is a filter plate 108 according to the present invention, of identical construction to lower plate 92 but positionally inverted with respect to the lower plate 92, to form interior sub-channels for liquid flow which are configured as shown in FIG. 11 when the stacked filter plate assembly of FIG. 10 is fully mated with respect to its constituent elements.

As shown, the upper filter plate 108 is configured with openings 109 and 110 communicating with the circumscribing channel surrounding the main flow channel on the plate. Opening 109 in this configuration is closed by a suitable plug, while opening 110 has a fluid introduction passage 111 in flow communication therewith, for feeding of a second liquid, e.g., dialysate solution, into the circumscribing channel (the direction of liquid feeding being indicated by the arrow P). From the circumscribing channel, the liquid enters the foraminous support through the edge openings 112 thereof and flows therethrough to the opposite side of the lower filter plate for discharge through openings 113 and 114 and out of the system through the fluid discharge passage 115 in the direction indicated by arrow Q. Circumscribing channel opening 114 of the lower filter plate is closed by a suitable plug in this arrangement. The stacked filter plate assembly may be retained on the rods 88–91 by suitable mechanical fasteners, such as washers 116–119 and respective lock-nuts 120–123. For such purpose, the rods 88–91 are suitably configured with threaded outer surfaces.

Figure 12:
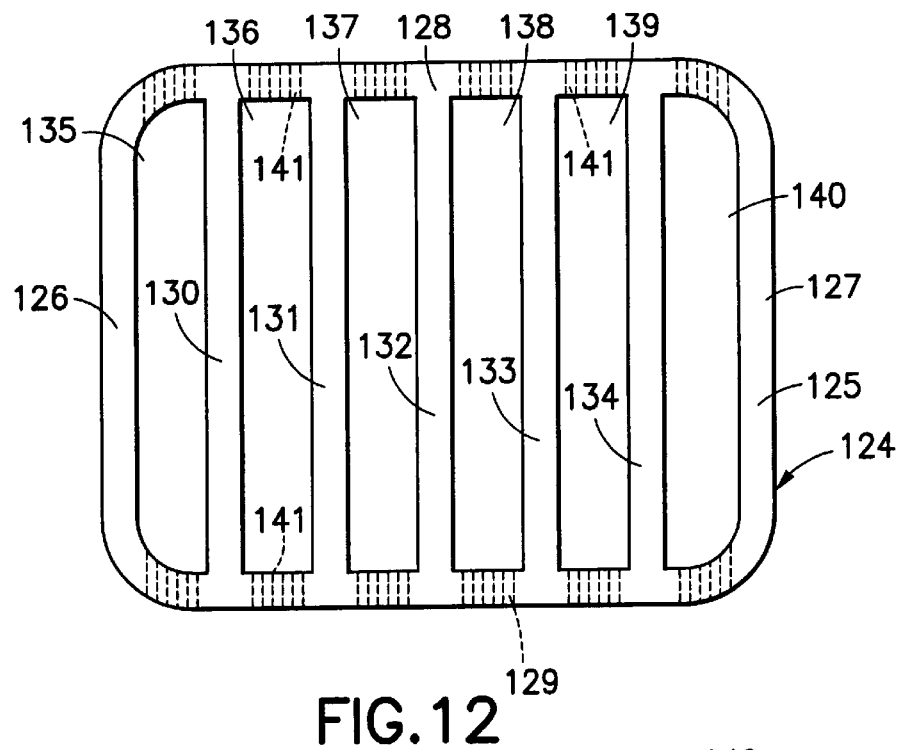
FIG. 12 is a plan view of a support for a unitary filter element that may be used in the stacked filter assembly component of the invention.

FIG. 12 is a plan view of a support for a unitary filter element that may be used in the invention. The support 124 includes a circumscribing frame 125 formed by the respective side portions 126–129. The circumscribing frame 125 is associated with an array of spaced-apart and substantially parallelly aligned ribs 130–134 extending between and joined at their opposite ends to the frame 125 (sides 128 and 129, respectively). The ribs 130–134 and frame 125 thus corporately form a series of corresponding substantially parallel filtrate flow channels 135–140 as shown. Openings 141 are provided in the frame 125 in liquid flow communication with the filtrate flow channels 135–140 for egress of filtrate from the filtrate flow channels 135–140 through the frame openings 141.

Figure 13:
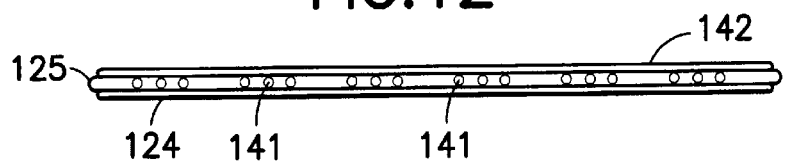
FIG. 13 is an edge elevation view of a unitary filter element of FIG. 12.
Figure 14:
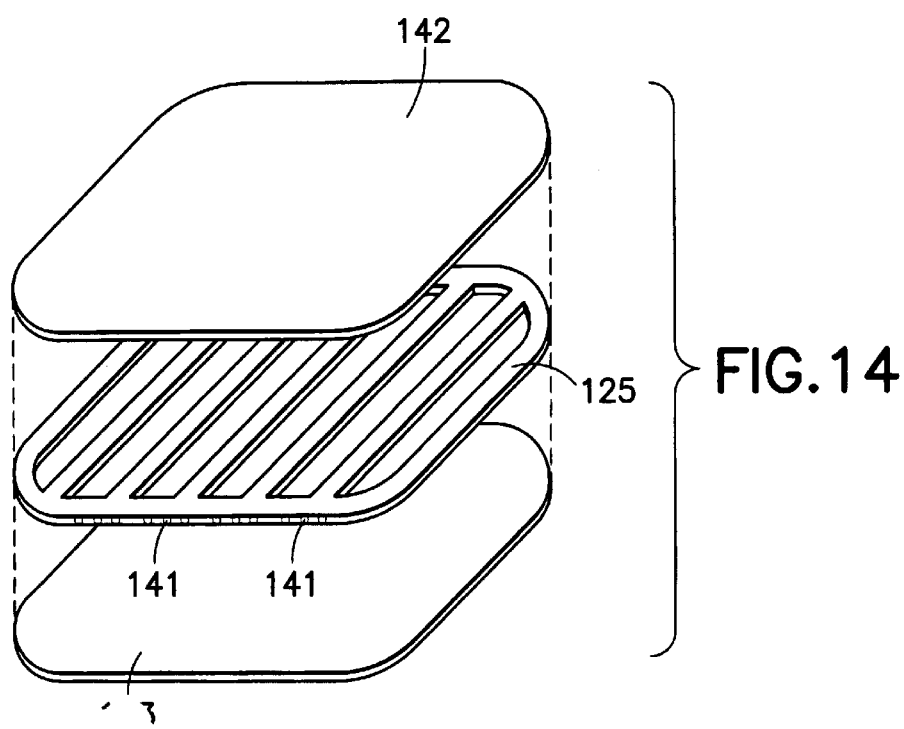
FIG. 14 is an exploded perspective view of the unitary filter element of FIG. 13.

FIG. 13 is an edge elevational view of the filter element comprising the support shown in FIG. 12. FIG. 14 is an exploded perspective view of the unitary filter element whose edge elevational view is shown in FIG. 13. The unitary filter element features a first filter sheet 142 which is continuously secured along its margins to a first face of the frame 125. Likewise, a second filter sheet 143 is continuously secured along its margins to a second face of the frame. When thus assembled, the first and second filter sheets together with the frame 125 define an enclosed interior volume comprising the filtrate channels separated by the ribs. Accordingly, filtrate entering the enclosed liquid volume through the first and second filter sheets, i.e., by permeation of liquid through the filter sheets, may flow in the filtrate flow channels and be discharged from the filter elements through the frame openings 141 which are in liquid communication with the filtrate flow channels 135–140.

The above-described unitary filter element may suitably be constructed and employed for short term filtration operation, e.g., on the order of about 6 months, following with the filter element may be discarded and replaced with a corresponding new element.

The unitary filter element may be formed of any suitable materials, such as for example polysulfone, polyvinylidene difluoride, polypropylene, nitrocellulose, polyethylene, and the like, as may be useful in the desired end use filtration application. The first and second filter sheets may be continuously secured along their margins to the respective first and second faces of the frame by any suitable joining or attachment method, including, but not limited to, ultrasonic welding, heat sealing, solvent welding, and adhesive bonding, as well as mechanical affixation.

It will be apparent from the preceding description that any number of paired filter plates, with interposed support element and filter sheets, may be assembled to form a cross-flow filter depending on the desired purpose of the culture system. The number of stacked filter plates in a specific filter system will be largely determined by space requirements and constraints, allowable pressure drop in the system, solids concentration and volumetric flow rate of the liquid to be filtered, and the filtration efficiency of the specific filter sheets employed.

In an embodiment having the dimensions for the filter plates previously described in connection with FIGS. 5–7 hereof, a superficial velocity of aqueous biomass suspension in the range of 1.5 meters per second through the flow channel defined between adjacent paired plates is readily accommodated, at a volumetric feed rate of approximately 1 liter of aqueous biomass suspension per minute in the flow channel, without any significant maldistribution of the liquid flow therein.

Incorporation of the stacked filter assembly comprising filter plates into the culture system of the present invention provides filtration that is highly hydraulically uniform in operation, without the existence of operational tendencies toward flow anomalies, such as bypassing, channeling, and "dead space" formations, which are found in stacked plate filters of the prior art.

Figure 15:
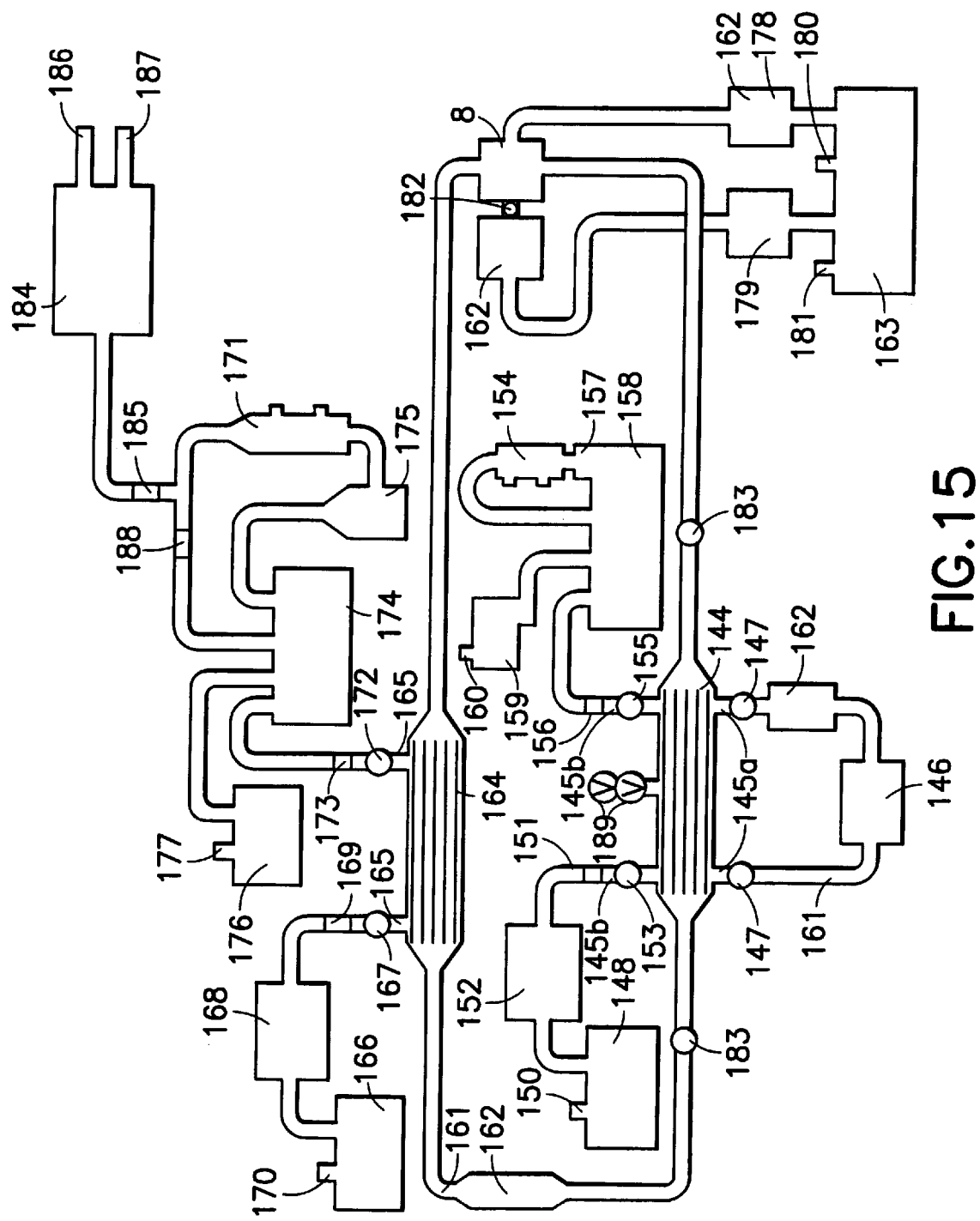
FIG. 15 is a schematic drawing of the microbial pathogen culturing system.

A preferred embodiment of the entire pathogen culturing system of the invention is shown schematically in FIG. 15. As indicated below, various components of the pathogen culturing system shown in this figure may be modified or used in more than one form to enable the desired system functions to be obtained. Larger scale cell culture efforts require additional filtration and growth capability for the added volume being handled. Different media or types of cells cultured may also require different types or numbers of filter systems to enable waste product removal, optimal cell growth and product harvest.

Referring now to FIG. 15, cells are grown in a tangential flow growth device 144 such as a hollow fiber or plate and frame device or a mass transfer culture system 3. Cells may be either of the suspension or exchange dependent type. The membrane porosity in the tangential flow device is selected by consideration of the growth requirements of the cell type. For example, for a cell type, which (a) grows anchored to the membrane and produces a product of 160,000 molecular weight, (b) produces and reacts to a coexpressed inhibitory substance that does not pass any molecular filter, a larger pore membrane such as one having a 0.2 micron pore size may be used. A growth chamber for a second cell type which (a) is an anchorage cell producing a 26,000 molecular weight product and no inhibitory substance and (b) growing in a serum-free medium, would better be equipped with a 10,000 molecular weight membrane.

Tangential flow growth device 144 as shown in FIG. 15 may have two or four permeate ports 145a or 145b. When there are only two permeate ports 145a they are used to connect the tangential flow growth device 144 to auxiliary reversible pump 146 for recirculation of the medium in the extracapillary space of the tangential flow growth device 144 in a permeate recirculation loop. This recirculation may be operated with or counter to the current in the main stream for better mixing. Valves or stopcocks 147 allow the medium flow to be stopped or started.

A second pair of permeate ports 145b allows substances to be added to the system from the auxiliary reservoir 148, for example, to cause the cells in the tangential flow growth device 144 to have increased yield or to produce a factor or byproduct, which may then be separated by ultrafilter 149.

The auxiliary reservoir 148 has a vent or extra port 150 for pressure release and a sterile filter 151 of a dead end type placed between auxiliary pump 152 and a valve or stopcock 153. The auxiliary pump 152 and reservoir 148 may be as simple as a standard syringe for the addition of supplements directly to the extracapillary space of the tangential flow growth device 144. The ultrafiltration scheme employing ultrafilter 154 allows the separation and concentration of both (1) suspension culture cells with any extracellular products retained by the given porosity of fibers used in the tangential flow growth device 144 and/or (2) extracellular products from anchorage dependent cells with some sluffed cells. A valve or stopcock 155 allows the tangential flow growth device 144 to be connected to the ultrafilter 154. A sterile dead end filter 156 is placed between the valve or stopcock 155 and ultrafilter 154, unless the cells being grown are the product to be harvested as when the product is ultracellular (for example, rabies virus). Ultrafilter 154 may be a microporous filter and/or an ultrafilter for separating and concentrating the extracapillary volume as required. An auxiliary pump 157 allows recirculating of the concentrate loop. An auxiliary reservoir 158 is for concentrating and separating the cellular byproducts. Another auxiliary reservoir 159 allows dialysis or cell washing or detergent treatment of a product such as a pathogen. An additional port 160 may be used for a vent.

Tangential flow growth device 144 may comprise multiple chambers that may be serially connected but preferably are in parallel because each chamber receives the same quality of nutrient supply when the chambers are in parallel. As discussed in detail above, tangential flow growth device 144 is attached to tubing 161 at each end that is of a size and manufacture appropriate for sterile production and flow. A four-way valve 8 connected to tubing 2 enables adjustment of medium flow direction through the tangential flow growth device 144.

Monitoring chambers 162 may comprise multiple ports and/or multiple chambers that concurrently monitor system parameters of parts of the system such as temperature, pH, $PO_2$, glucose, etc. Such monitoring may also be performed at the main reservoir 163. This monitoring may be implemented by computerization as has been developed for other systems to measure and adjust system conditions and may be used to compare different valves of particular parameters at different monitoring chambers 162 within the system.

A sterile barrier tangential flow membrane device 164, which is nonrestrictive for flow or pressure as well as having a low coefficient of absorption and adsorption for extracellular products is connected to the tangential flow growth device by means of tubing 161. The sterile barrier tangential flow membrane device 164 may comprise semipermeable membranes in the form of hollow fibers or the stacked plate filter system discussed above.

The stacked plate device can be comprised of sequential chambers of different membrane types to effect different membrane separations in a discrete system. For example, the stacked plate device may comprise a membrane for ammonia removal, and a subsequent membrane for immunoglobulin removal would be highly useful in immunoglobulin production for diagnostic kits. In other words, the sterile barrier tangential flow membrane device 164 can be comprised of multiple chambers each of which is independent of the other and has its own specific membrane type and permeate ports 165. All of the chambers of 164 are housed in a singular unit having only one inlet and one outlet port. The flow through the chambers would be in a serpentine path created by the installation of another base plate 87 (FIG. 10) between each of the chambers of different membrane types.

Two permeate ports 165 are shown on the sterile barrier tangential flow device 164 in FIG. 15. One of these permeate ports 165 is connected to auxiliary nutrient tank 166. A valve or stopcock 167 allows media or extra nutrient to be pumped by auxiliary pump 168 from the nutrient tank 166 through sterile filter 169, a dead end type filter of the appropriate size. Port 170 allows further media or nutrient addition to nutrient tank 166.

The second permeate port 165 on the sterile barrier tangential flow device 164 is connected to ultrafilter 171 in FIG. 15. Ultrafilter 171 allows separation and concentration of an extracellular product that is secreted by the cells and that passed through the pores of devices 144 and 164. Valve or stopcock 172 controls connection of ultrafilter 171 to the system. Sterile filters 151, 156, 169 and 173 are back up protective devices which aid in the maintenance of a sterile environment. These devices should not pose a barrier to the desired product but only to contaminants. These devices cannot replace good sterile techniques. Obviously, where good sterile technique is used these filters are not necessary. Auxiliary tank 174 allows concentration of extracellular products such as IgG, hormones and HIV virus, and auxiliary pump 175 is used to recirculate spent medium in the concentration loop. Auxiliary reservoir 176 connected to auxiliary tank 174 allows dialysis of concentrated extracellular metabolites and viruses and has a port 177 useful to add dialysate or to vent the system.

Preferably an open structure of 0.2 micron membranes is used for tangential flow growth device 144 and sterile barrier tangential flow membrane device 164. Finer membranes (molecular weight) may be placed at these locations if this does not restrict growth of the cells being grown. In addition, multiple chambers can be placed at the location of each tangential flow device 144 and 164 shown in FIG. 15 to be linked in parallel with each other.

The filters in the microbial pathogen culturing system of the invention allows inhibitory substances and non-essential cell by-products to be filtered out of the medium while retaining cell-stimulatory substances. Alternatively, or in addition, the spent medium may be dialyzed against a medium containing concentrated glucose and desirable salts using the stacked plate filter of the previous invention. Media is circulated from main reservoir 163 through the main system by recirculating pump 178. A gas permeator chamber 179 is utilized for replenishment of oxygen, for pH control by utilizing carbon dioxide, or for the addition of other required gas or gases. The main reservoir may be provided with one or more sterile vents 180 and ports 181.

Main valve 182 allows the culture system to be back pressured as required to enhance mass transfer. Valves, stopcocks or clamps 183 may be used to isolate the tangential flow growth device 144 from the rest of the system.

Removal of Medium Components

The cell production of viruses and thus, density of viruses in the medium may be increased by removal of inhibitory substances, such as cellular metabolites, from the culture medium. Removal of the spent medium from a microbial pathogen culture system may be accomplished by a number of methods. In many systems now used, removal is accomplished by simply opening a valve. Disadvantages of such a system are that (1) contaminants may come into the culture system through the opening; (2) useful medium components and desirable end products of the system are removed from it; and (3) pathogenic viruses are prematurely released from the system with resulting exposure of laboratory personnel to the hazard. To avoid some or all of these problems, a series of filters may be provided as a filter barrier when the valve is opened. A filter barrier of about 0.2 u pore size still allows desirable soluble end products and viruses out of the system but does not allow bacteria in or out, or allow out any particulate end products such as cell walls that have a size greater than 0.2 u. Use of a smaller filter (molecular sieve) allows end products such as urea, ammonia, creatinine and small carbohydrates to escape but retains viruses and cells. Filters with pore sizes between these primary types allow finer discrimination between particular sizes of medium components.

Lysing Chamber

The reduced volume of concentrated viral suspension is transferred under sealed conditions in previously connected sterile tubing from the filter to the lysing chamber or harvest vessel.

The means for harvesting the culture product preferably comprises a harvest vessel 174 as is shown in FIG. 15 that is leak-proofly connected to the mass transfer culture system by a harvest line. During growth of the cells and until the desired time of harvest the harvest line connecting the vessel to the mass transfer culture system is closed by valve 185. When the harvest line is opened by a valve means, culture medium containing pathogens, spent medium and waste products begins to flow toward the reservoir. Prior to the opening of valve 185, the previously used filter system for solids filtration and means for nutrient exchange may be used to remove excess medium and undesirable components prior to entry of the medium into the harvest line. Alternatively, filtration and nutrient exchange means may be provided on the harvest line so that medium is treated prior to flowing into the harvest vessel. Detergent or other pathogen-destroying substance is then added aseptically to the treated, reduced-in-volume, pathogen-containing medium in the harvest vessel by means of a valve on a line 186 connected to reservoir of the pathogen destroying substance (not shown). Treatment regimes for pathogenic viruses or other pathogens using detergents or other substances to destroy all pathogenic activity are well known. Thus one standard treatment comprises addition of Nonident P40™ (Sigma Chemical, St. Lous, Mo.) according to standard manufacturer's instructions. Following the appropriate treatment, the outlet port of the vessel may be opened to remove the unhazardous pathogen product for its intended use.

All of the steps for growing viruses, between the initial inoculation of the mass transfer culture tube and the removal of the viral particles from the last filter are done under sealed conditions with all viable viruses being completely contained within the system. When the system is opened, the laboratory worker and the laboratory are only exposed to noninfective viral particles. Thus laboratory contamination and workers exposure to infective viruses are minimized. The sealed pathogen culturing system into which cell culture nutrients may be aseptically added and from which undesirable end products may be removed while increasing cell production of the pathogens within the system, allows high concentrations of pathogen to be obtained in a small confined laboratory area without opening the system or removing pathogens. All sampling, monitoring, and medium adjustments may be performed automatically and aseptically. When the appropriate amount of time has elapsed to yield the desired pathogen concentration, the system may be manually or automatically changed from the cell growth to the product harvest phase by appropriate valve means adjustments.

The features and advantages of the present invention will be more clearly understood by reference to the following examples, which are not to be construed as limiting the invention.

EXAMPLE I

Cell growth. A hollow fiber mass transfer culture system is constructed as described in U.S. patent application Ser. No. 06/936,486. This system is sterilized with hypochlorite solution and rinsed with sterile deionized water using standard procedures. The bioreactor is then filled with cell culture medium, RPMI 1640 (Rochester Park Memorial Institute medium) plus 5% fetal calf serum, and incubated for 48 hours at 37 degrees C in a 5% carbon dioxide, no humidity environment, as a check for sterility and system equilibration.

Using standard cell culture techniques, an inoculum of cell type EL-4-IL-2 is prepared from stock cultures and inoculated into the extracapillary space of the hollow fiber bioreactor. The system is again incubated for 20 days with media being changed as required in accordance with prior practice for this cell type. The four-way LL valve is switched each half hour during the working day and once each night, usually about midnight, taking care to use alternate positioning on successive nights.

Resulting cell growth in the bioreactor as determined by visual observation of turbidity of the liquid containing the suspension culture is equally dispersed throughout the growth chamber after incubation as described.

Other cell types, including BALB-3T3 and *Mycoplasma galasepticum,* grown in standard media as described in the above-cited patent application, and observed microscopically also are found to be uniformly dispersed throughout the growth chamber. Use of sterile barrier tangential flow devices (Microgon, Inc., Languna Hills, Calif.) as well as dual valve arrangements allowed a sterile environment to be maintained over extended time periods in spite of numerous nutrient media exchanges and sample withdrawals.

EXAMPLE II

Culture system inoculation. The mass transfer culture tube is inoculated with a concentrated suspension of virus-infected cells. In the preferred embodiment three to ten ml of a suspension having about $10^6$ cells per ml is added aseptically by using a syringe to inject inoculum through a septum at port 189. Alternatively, port 189 comprises a double valve assembly as described above (see discussion of double valve assemblies 17 and 20) and the culture inoculum is introduced aseptically following sterilization of the outer valve. It is clear that a wide range of volumes and concentrations of cells may be used, with the ideal inoculum providing a sufficient number of cells to multiply and produce large numbers of progency viruses but not so many cells as will be overburden and clog the system. Inoculum preparation and aseptic handling of cell cultures is well known in the art and is not part of the invention.

EXAMPLE III

Harvest of progency viruses. As an example of viral harvest, a viral suspension is washed of medium components by using the stacked filter plate components of the invention. Stacked filter plates may be assembled with one or more filter papers that will allow differential separations by size, molecular weight, ionic charge, hydrophilicity, hydrophobicity, antigen antibody complexing, or other membrane separable characteristics. In the sequential chambers of the flat plate device is a membrane capable of passing low molecular weight substances having an ionic charge such as urea and ammonia. A suitable filter is the Charge Mosaic™ (TOSOH, Tokyo, Japan). In a second chamber is a filter paper that will allow proteins and other macromolecules but not viruses to pass through. Suitable filters include the MX-100K™ (Membrex, Garfield, N.J.), and the TSK-1000K™ (TOSOH, Tokyo, Japan). In the third chamber is a membrane capable of sterilizing nutrient media additions. A suitable filter is Durapore® (Millipore, Bedford, Mass.). Other sequential chambers may be added as deemed appropriate for particular applications and functions, such as adding glucose, removing creatinin, or harvesting immunoglobulins.

To obtain progency viruses for harvesting, 100 liters of medium (RPMI 1640, Example I) plus 5% fetal calf serum is placed in the main reservoir 163 of the tangential flow growth device 144. The tangential flow growth device 144 is inoculated with an HIV-infected cell line through port 189 (Example II). The culture is allowed to grow until the consumption of nutrients has ceased. The incubation time depends on environmental parameters and inoculum size and viability but may be in the order of four days for a suitable progency concentration to be attained. At the termination of incubation, valve 172 is opened. The virus-rich medium is transferred by pumping action of the system (recirculating pump 178) and partial closure of main valve 182 causes the liquid to be forced through sterile barrier tangential flow device 164 into auxiliary tank 174, so that essentially all of the 100-liter liquid volume is transferred to tank 174. While valve 185 remains closed (it is closed during the culture growth and incubation period) and valve 188 is open, auxiliary pump 175 is turned on and valve 172 is closed. The ports on ultrafilter 171 are opened so that liquid separated from the viruses is pumped through ultrafilter 171 and out of the system. The product viruses remain in the system and are increasingly concentrated until they are suspended in about 5 liters of liquid. Valve 188 is then closed so that the remaining 5 liters of liquid are transferred into vessel 184. Port 186 is then opened and detergent or other virus-destroying chemical is added at the manufacturer's recommended concentration. Vessel 184 contains a magnetic stirring bar or may be otherwise equipped for agitation of the contents to mix the detergent into the virus suspension as appropriate for the virus treatment. After the virus particles are rendered harmless, port 187 is opened to remove the uninfected end-product for any desired experimentation or use.

The detergent treatment or other pathogen treatment may alternatively be done in auxiliary tank 174 without withdrawing the liquid to vessel 184, but removal of the liquid to vessel 184 allows the remaining growth portion of the system to continue being used or to be treated or cleaned for other uses. Because of the multiple chamber potential of tangential flow sterile barrier device 164, the functions of ultrafilter 171, auxiliary tank 174 and auxiliary pump 175 may be accomplished by tangential flow sterile barrier device 164 in batching operations where continuous culture is not desired.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A mass transfer system comprising:
   (a) a first tangential flow membrane device comprising:
      i) a first housing enclosing an interior volume;
      ii) one or more filter means separating the interior volume of the first housing into two or more chambers, including a first set of chambers comprising an intra-filter volume and a second set of chambers comprising an extra-filter volume;
   (b) a second tangential flow membrane device in fluid communication with one or more of the chambers of the first tangential flow membrane device, said second tangential flow membrane device comprising:
      i) a second housing enclosing an interior volume;
      ii) one or more filter means separating the interior volume of the second housing into two or more chambers, including a first set of chambers comprising an intra-filter volume and a second set of chambers comprising an extra-filter volume;
   (c) one or more substance addition means in fluid communication with the extra-filter volume or intra-filter volume of the first and/or second tangential flow membrane device; and
   (d) one or more fluid exit means in fluid communication with the extra-filter volume or intra-filter volume of the first and/or second tangential flow device.

2. The mass transfer system of claim 1 wherein a first group of one or more chambers of the first tangential flow membrane device are connected in loop fluid communication with a first group of one or more chambers of the second tangential flow membrane device such that fluid exiting the first group of one or more chambers of the first tangential flow membrane device flows into the first group of one or more chambers of the second tangential flow membrane device, and fluid exiting first group of one or more chambers of the second tangential flow membrane device flows into the first group of one or more chambers of the first tangential flow membrane device.

3. The mass transfer system of claim 1 wherein the first and/or second tangential flow membrane device comprises multiple filter means in serial connection.

4. The mass transfer system of claim 1 wherein the first and/or second tangential flow membrane device comprises multiple filter means in parallel connection.

5. The mass transfer system of claim 1 wherein the filter means comprises one or more flat sheet filter.

6. The mass transfer system of claim 1 wherein the filter means comprises one or more hollow fiber filters.

7. The mass transfer system of claim 1 further comprising a means for redirecting the flow of fluid in the intra-filter volume.

8. The mass transfer system of claim 1 further comprising a means for redirecting the flow of fluid in the extra filter volume.

9. The mass transfer system of claim 1 wherein the filter means of the first and/or second tangential flow membrane device comprises a plurality of filter means.

10. The mass transfer system of claim 1 further comprising a reservoir in fluid communication with the substance addition means.

11. The mass transfer system of claim 10 wherein the reservoir contains a fluid comprising a growth medium for a culturable organism.

12. The mass transfer system of claim 10 wherein the reservoir contains a fluid comprising a buffer.

13. The mass transfer system of claim 1 further comprising means for circulating fluid through the intra-filter volume or extra-filter volume of the first and/or second tangential flow device.

14. The mass transfer system of claim 13 wherein the circulating fluid comprises a growth medium for a culturable organism.

15. The mass transfer system of claim 13 wherein the circulating fluid comprises a buffer.

16. The mass transfer system of claim 13 wherein the means for circulating fluid comprises a reversible or non-reversible pump operationally interposed in the path of fluid communication:
   (a) which exits the intra-filter volume at a first position of the housing and enters the intra-filter volume at a second position of the housing; or which
   (b) exits the extra-filter volume through a first position of the housing and enters the exit-filter volume through a second position of the housing.

17. The mass transfer system of claim 16 further comprising at least one valve interposed in the path of fluid communication between the pump and the first and/or second tangential flow device.

18. The mass transfer system of claim 13 further comprising a means for changing the direction of flow of fluid in the extra-filter volume or in the intra-fiber volume.

19. The mass transfer system of claim 13 further comprising a reservoir arranged in a loop path of fluid communication:
   (a) which exits the intra-filter volume at a first position of the housing and enters the intra-filter volume at a second deposition of the housing; or which
   (b) exits the extra-filter volume through a first position of the housing and enters the exit-filter volume through a second position of the housing.

20. The mass transfer system of claim 19 wherein the reservoir has a vent for releasing pressurized fluid from the reservoir.

21. The mass transfer system of claim 20 wherein the vent is fitted with a sterile filter for filtering released fluid.

22. The mass transfer system of claim 19 wherein the reservoir comprises one or more ports therein for addition and/or removal of fluid.

23. The mass transfer system of claim 22 wherein one or more of the ports are each fitted with a sterile filter for filtering the fluid.

24. The mass transfer system of claim 13 wherein means for circulating fluid comprises:
  (a) a means for recirculating fluid in the intra-fiber volume of the first and/or second housing comprising:
    i) a means for providing a path of fluid communication for removing fluid from a first portion of the intra-fiber volume of the first housing and reintroducing said fluid to a second portion of the intra-fiber volume of the first housing; and
    ii) a pump operationally interposed in the path of fluid communication of (a)i); and/or
  (b) a means for circulating fluid in the extra-fiber volume of the first and/or second housing comprising:
    i) a means for providing a path of fluid communication for removing fluid from a first portion of the extra-fiber volume of the first housing and reintroducing said fluid to a second portion of the extra-fiber volume of the first housing; and
    ii) a pump operationally interposed in the path of the flow communication of (b)i).

25. The mass transfer system of claim 24 further comprising a reservoir interposed in the path of fluid communication of 43(a)ii) and/or 43(b)ii).

26. The mass transfer system of claim 24 wherein the reservoir has a vent for releasing pressurized fluid from the reservoir.

27. The mass transfer system of claim 24 wherein the vent is fitted with a sterile filter for filtering released fluid.

28. The mass transfer system of claim 24 wherein the reservoir comprises one or more ports for adding fluid to the reservoir and/or removing fluid from the reservoir.

29. The mass transfer system of claim 28 wherein the ports are fitted with a sterile filter for filtering fluid as it is removed from and/or added to the reservoir.

30. The mass transfer system of claim 24 wherein the circulating fluid comprises a growth medium for a culturable organism.

31. The mass transfer system of claim 24 wherein the circulating fluid comprises a buffer.

32. The mass transfer system of claim 24 wherein the a pump of 43(a)ii) and/or 43(b)ii) is a reversible pump.

33. The mass transfer system of claim 1 further comprising a means for the addition of one or more gasses to the extra-filter space of the first and/or second tangential flow membrane device.

34. The mass transfer system of claim 33 where the means for the addition of one or more gasses is fitted with a sterile filter for filtering gas.

35. The mass transfer system of claim 26 further comprising one or more ultrafilter devices, each arranged in fluid communication with the extra-filter volume and/or the intra-filter volume of the first and/or second tangential flow membrane device.

36. The mass transfer system of claim 35 wherein the ultrafilter device comprises:
  a) a reservoir;
  b) a tangential flow membrane device (the "ultrafilter") in loop fluid communication with the reservoir, suitable for concentrating cells, metabolites of cells and/or virus; and
  c) a means for removing a liquid from the reservoir and forcing the liquid through the ultrafilter and back to the reservoir with sufficient power to generate an ultrafiltrate stream.

37. The mass transfer system of claim 36 wherein the means for removing the liquid from the reservoir and forcing the liquid through the ultrafilter comprises a pump.

38. The mass transfer system of claim 36 further comprising a means for removing ultrafiltrate from the ultrafiltrate device.

39. The mass transfer system of claim 38 where the means for adding and removing ultrafiltrate is fitted with a sterile filter for filtering ultrafiltrate as it is removed from the ultrafiltrate device.

40. The mass transfer system of claim 36 wherein the reservoir is equipped with means for adding and/or removing fluid.

41. The mass transfer system of claim 40 wherein the means for adding and removing fluids is fitted with a sterile filter for filtering fluid as it is added and/or removed from the reservoir.

42. The mass transfer system of claim 36 wherein the reservoir is equipped with a vent for releasing pressurized fluid from the reservoir.

43. A mass transfer system comprising:
  (a) a first tangential flow membrane device comprising:
    i) a first housing enclosing an interior volume;
    ii) one or more filter means separating the interior volume of the first housing into one or more extra-filter chambers and one or more intra-filter chambers;
  (b) one or more substance addition means in fluid communication with one or more of the chambers of the first and or second tangential flow membrane device;
  (c) a second tangential flow membrane device in fluid communication with one or more of the chambers of the first and/or second tangential flow membrane device, said second tangential flow membrane device comprising:
    i) a second housing enclosing an interior volume;
    ii) one or more filter means separating the interior volume of the second housing into one or more extra-filter chambers and one or more intra-filter chambers; and
  (d) a fluid exit means in fluid communication with the first and or second tangential flow membrane device;
wherein a first set of one or more chambers of the first tangential flow membrane device are connected in loop fluid communication with a first set of one or more chambers of the second tangential flow membrane device such that fluid exiting the first set of one or more chambers of the first tangential flow membrane device flows into the first set of one or more chambers of the second tangential flow membrane device, and fluid exiting first set of one or more chambers of the second tangential flow membrane device flows into the first set of one or more chambers of the first tangential flow membrane device.

44. The mass transfer system of claim 43 wherein the first and/or second tangential flow membrane device is configured to operate as a sterile barrier device.

45. The mass transfer system of claim 43 further comprising a means for adding one or more gasses to the extra-filter space of the first and/or second tangential flow membrane device.

46. A mass transfer system, comprising:
  (a) a medium reservoir containing a growth medium;
  (b) a tangential flow growth device in fluid connection with the medium reservoir comprising:
    i) a first housing enclosing an interior volume;
    ii) one or more filter means separating the interior volume of the first housing into one or more extra-filter chambers and one or more intra-filter chambers;

(c) a pump system operationally positioned in the path of fluid communication between the reservoir and the tangential flow growth device, for pumping the medium from the reservoir to the tangential flow growth device;

(d) a sterile barrier tangential flow membrane device connected in fluid communication with one or more of the extra-filter chambers or the intra filter chambers of the tangential flow growth device comprising:
 i) a second housing enclosing an interior volume;
 ii) one or more filter means separating the interior volume of the second housing into one or more extra-filter chambers and one or more intra-filter chambers; and (e) a means for monitoring medium conditions in the medium reservoir.

47. A mass transfer system, comprising:

(a) a medium reservoir containing a growth medium;

(b) a tangential flow growth device connected to the medium reservoir comprising:
 i) a fist housing enclosing an interior volume;
 ii) one or more filter means separating the interior volume of the first housing into one or more extra-filter chambers and one or more intra-filter chambers;

(c) a pump system having discharge and inlet ports for pumping the medium from the reservoir to the tangential flow growth device;

(d) a sterile barrier tangential flow membrane device connected in fluid communication with one or more of the extra-filter chambers or the intra filter chambers of the tangential flow growth device comprising:
 i) a second housing enclosing an interior volume;
 ii) one or more filter means separating the interior volume of the second housing into one or more extra-filter chambers and one or more intra-filter chambers; and (e) a means for monitoring medium conditions in the medium reservoir; and (f) a tangential flow filtering device in fluid communication with the medium reservoir for concentrating and/or dialysis of the medium.

48. A mass transfer system, comprising:

(a) a medium reservoir containing a growth medium;

(b) a tangential flow growth device connected to the medium reservoir comprising:
 i) a first housing enclosing an interior volume;
 ii) one or more filter means separating the interior volume of the first housing into one or more extra-filter chambers and one or more intra-filter chambers;

(c) a pump system having discharge and inlet ports for pumping the medium from the reservoir to the tangential flow growth device;

(d) a sterile barrier membrane device connected in fluid communication with one or more or the extra-filter chambers of the tangential flow growth device comprising:
 i) a second housing enclosing an interior volume;
 ii) one or more filter means separating the interior volume of the second housing into one or more extra-filter chambers and one or more intra-filter chambers; and (e) a means for monitoring medium conditions.

49. A mass transfer system, comprising:

(a) a medium reservoir containing a growth medium;

(b) a tangential flow growth device connected in fluid communication with the medium reservoir comprising:
 i) a housing enclosing an interior volume;
 ii) one or more filter means separating the interior volume of the first housing into one or more extra-filter chambers and one or more intra-filter chambers;

(c) a pump system, operationally interposed in a path of fluid communication between the reservoir and the tangential flow growth device, for pumping the medium from the reservoir to the tangential flow growth device;

(d) a means for monitoring medium conditions; and (e) an auxiliary flow circuit comprising an auxiliary pump, joined in fluid communication with the tangential flow growth device and arranged for flowing cell culture from the tangential flow growth device through the auxiliary circuit for recirculation thereof.

50. A mass transfer system, comprising:

(a) a medium reservoir containing a growth medium;

(b) a tangential flow growth device connected in fluid communication with the medium reservoir comprising:
 i) a housing enclosing an interior volume;
 ii) one or more filter means separating the interior volume of the first housing into one or more extra-filter chambers and one or more intra-filter chambers;

(c) a pump system operationally interposed in a path of fluid communication between the reservoir and the tangential flow growth device, for pumping the medium from the reservoir to the tangential flow growth device;

(d) a means for monitoring medium conditions; and (e) an auxiliary flow circuit comprising an auxiliary pump and auxiliary reservoir, joined in fluid communication with the tangential flow growth device and arranged for flowing cell culture from the tangential flow growth device through the auxiliary circuit for recirculation thereof.

51. A mass transfer system, comprising:

(a) a medium reservoir containing a growth medium;

(b) a tangential flow growth device comprising:
 i) a first housing enclosing an interior volume;
 ii) one or more hollow fiber filters separating the interior volume of the first housing into one or more extra-fiber chambers and one or more intra-fiber chambers;

(c) a pump system operationally positioned in a path of fluid communication between the reservoir and the tangential flow growth device for pumping the medium from the reservoir to the tangential flow growth device;

(d) a sterile barrier membrane device connected in fluid communication with one or more of the extra-fiber chambers of the tangential flow growth device comprising:
 i) a second housing enclosing an interior volume;
 ii) one or more filter means separating the interior volume of the second housing into one or more extra-filter chambers and one or more intra-filter chambers; and (e) a means for monitoring medium conditions; and (f) a tangential flow filter device arranged in fluid communication with the medium reservoir for concentrating and/or dialysis of the medium.

52. A mass transfer system, comprising:

(a) a medium reservoir containing a growth medium;

(b) a sterile barrier tangential flow membrane device comprising;
  i) a housing enclosing an interior volume;
  ii) one or more filter means separating the interior volume of the first housing into one or more extra-filter chambers and one or more intra-filter chambers;

(c) a pump system operationally positioned in a path of fluid communication between the reservoir and the tangential flow growth device for pumping the medium from the reservoir to the sterile barrier tangential flow membrane device; and (d) a means for monitoring medium conditions.

53. A mass transfer system, comprising:

(a) a medium reservoir containing a growth medium;

(b) a sterile barrier tangential flow membrane device comprising:
  i) a first housing enclosing an interior volume;
  ii) one or more filter means separating the interior volume of the first housing into one or more extra-filter chambers and one or more intra-filter chambers;

(c) a pump system operationally positioned in a path of fluid communication between the reservoir and the tangential flow growth device for pumping the medium from the reservoir to the sterile barrier tangential flow membrane device;

(d) a means for monitoring medium conditions; and (e) a tangential flow filter device for concentrating and/or dialysis of the medium removed via the sterile barrier tangential flow membrane device comprising:
  i) a second housing enclosing an interior volume;
  ii) one or more filter means separating the interior volume of the second housing into one or more extra-filter chambers and one or more intra-filter chambers.

54. A mass transfer system, comprising:

(a) a medium reservoir containing a growth medium;

(b) a tangential flow growth device connected to the medium reservoir comprising:
  i) a housing enclosing an interior volume;
  ii) one or more filter means separating the interior volume of the first housing into one or more extra-filter chambers and one or more intra-filter chambers;

(c) a pump system operationally positioned in a path of fluid communication between the reservoir and one or more chambers of the tangential flow growth device for pumping the medium from the reservoir to the tangential flow growth device;

(d) a means for circulating the fluid in the extra-capillary space of the tangential flow culture device; and (e) means for monitoring medium conditions.

55. A mass transfer system, comprising:

(a) a medium reservoir containing a growth medium;

(b) a tangential flow growth device connected to the medium reservoir comprising:
  i) a first housing enclosing an interior volume;
  ii) one or more filter means separating the interior volume of the first housing into one or more extra-filter chambers and one or more intra-filter chambers;

(c) a pump system operationally positioned in a path of fluid communication between the reservoir and the tangential flow growth device for pumping the medium from the reservoir to the tangential flow growth device;

(d) a means for circulating the fluid in the extra-capillary space of the tangential flow culture device;

(e) a reservoir for the fluid in the extra-capillary space of the tangential flow culture device;

(f) a means of removing the fluid in the extra-capillary space;

(g) a means for monitoring medium conditions; and (h) a tangential flow filter device in fluid communication with the medium reservoir for concentrating and/or dialysis of the medium comprising:
  i) a second housing enclosing an interior volume;
  ii) one or more filter means separating the interior volume of the second housing into one or more extra-filter chambers and one or more intra-filter chambers.

56. A mass transfer system, comprising:

(a) a medium reservoir containing a growth medium;

(b) a tangential flow growth device connected to the medium reservoir comprising:
  i) a first housing enclosing an interior volume;
  ii) one or more filter means separating the interior volume of the first housing into one or more extra-filter chambers and one or more intra-filter chambers;

(c) a pump system operationally positioned in a path of fluid communication between the reservoir and the tangential flow growth device for pumping the medium from the reservoir to the tangential flow growth device;

(d) a means for circulating the fluid in the extra-capillary space of the tangential flow culture device;

(e) a reservoir for the fluid and cells in the extra-capillary space of the tangential flow culture device;

(f) a means of removing fluid from the extra-capillary space that includes a sterile barrier filter a means for monitoring medium conditions; and (g) a tangential flow filter device in fluid communication with the medium reservoir for concentration and/or dialysis of the medium comprising:
  i) a second housing enclosing an interior volume;
  ii) one or more filter means separating the interior volume of the second housing into one or more extra-filter chambers and one or more intra-filter chambers.

* * * * *

UNITED STATES PATENT AND TRADEMARK OFFICE
CERTIFICATE OF CORRECTION

PATENT NO : 6,127,141
DATED : Oct. 3, 2000
INVENTOR(S) : Henry B. Kopf

It is certified that error appears in the above-identified patent and that said Letters Patent are hereby corrected as shown below:

Column 25, line 22 change "fist" to - - first - -.

Signed and Sealed this

Twenty-second Day of May, 2001

Attest:

NICHOLAS P. GODICI

Attesting Officer

Acting Director of the United States Patent and Trademark Office